United States Patent
Peck et al.

(10) Patent No.: US 6,703,017 B1
(45) Date of Patent: Mar. 9, 2004

(54) REVERSAL OF INSULIN-DEPENDENT DIABETES BY ISLET-PRODUCING STEM CELLS, ISLET PROGENITOR CELLS AND ISLET-LIKE STRUCTURES

(75) Inventors: Ammon B. Peck, Gainesville, FL (US); Janet Cornelius, Gainesville, FL (US); Vijayakumar K. Ramiya, Gainesville, FL (US)

(73) Assignees: Ixion Biotechnology, Inc., Alachua, FL (US); University of Florida, Gainesville, FL (US)

(*) Notice: Subject to any disclaimer, the term of this patent is extended or adjusted under 35 U.S.C. 154(b) by 0 days.

(21) Appl. No.: 09/406,253

(22) Filed: Sep. 27, 1999

Related U.S. Application Data

(63) Continuation-in-part of application No. 08/547,746, filed on Oct. 25, 1995, now Pat. No. 6,001,647, which is a continuation-in-part of application No. 08/432,434, filed on Apr. 28, 1995, now abandoned, which is a continuation-in-part of application No. 08/234,071, filed on Apr. 28, 1994, now Pat. No. 5,834,308.

(51) Int. Cl.$^7$ .................................. C12N 5/00
(52) U.S. Cl. .................. 424/93.7; 435/366; 435/382; 435/371
(58) Field of Search .................. 435/366, 382, 435/371; 424/93.7

(56) References Cited

U.S. PATENT DOCUMENTS

| | | |
|---|---|---|
| 4,439,521 A | 3/1984 | Archer et al. |
| 4,696,286 A | 9/1987 | Cochrum |
| 4,902,295 A | 2/1990 | Walthall et al. |
| 4,935,000 A | 6/1990 | Dudek |
| 4,946,438 A | 8/1990 | Reemtsma et al. |
| 4,963,489 A | 10/1990 | Naughton et al. |
| 4,997,443 A | 3/1991 | Walthall et al. |
| 5,227,298 A | 7/1993 | Weber et al. |
| 5,387,237 A | 2/1995 | Fournier et al. |
| 5,425,764 A | 6/1995 | Fournier et al. |
| 5,429,821 A | 7/1995 | Dorian et al. |
| 5,443,950 A | 8/1995 | Naughton |
| 5,470,731 A | 11/1995 | Cochrum |
| 5,529,914 A | 6/1996 | Hubbell et al. |
| 5,531,997 A | 7/1996 | Cochrum |
| 5,573,934 A | 11/1996 | Hubbell et al. |
| 5,646,035 A | 7/1997 | Coon et al. |
| 5,656,468 A | 8/1997 | Dorian et al. |
| 5,672,361 A | 9/1997 | Halberstadt et al. |
| 5,674,289 A | 10/1997 | Fournier et al. |
| 5,780,021 A | 7/1998 | Sobel |
| 5,795,570 A | 8/1998 | Weber et al. |
| 5,824,331 A | 10/1998 | Usala |
| 5,830,492 A | 11/1998 | Usala |
| 5,834,005 A | 11/1998 | Usala |
| 5,849,285 A | 12/1998 | Selawry |
| 5,855,616 A | 1/1999 | Fournier et al. |
| 5,858,746 A | 1/1999 | Hubbell et al. |
| 5,861,313 A | 1/1999 | Pang et al. |
| 5,863,531 A | 1/1999 | Naughton et al. |
| 5,874,099 A | 2/1999 | Dionne et al. |
| 5,916,585 A | 6/1999 | Cook et al. |
| 5,958,404 A | 9/1999 | Selawry |
| 6,015,609 A | 1/2000 | Chaouk et al. |
| 6,022,743 A | 2/2000 | Naughton et al. |

FOREIGN PATENT DOCUMENTS

| | | |
|---|---|---|
| EP | 0 363 125 | 2/1989 |
| WO | WO00/09666 | 2/0000 |
| WO | WO86/01530 | 3/1986 |
| WO | WO91/09119 | 6/1991 |
| WO | WO93/00441 | 1/1993 |
| WO | WO94/23572 | 10/1994 |
| WO | WO00/02600 | 1/2000 |
| WO | WO00/02999 | 1/2000 |

OTHER PUBLICATIONS

Serup et al., "The homeodomain protein IPF–1/STF–1 is expressed in a subset of islet cells and promotes rat insulin 1 gene expression dependent on an intact E1 helix–loop–helix factor binding site", Biochem. J. 310:997–1003, (1995).

Rosenberg, "In Vivo Cell Transformation: Neogenesis of Beta Cells from Pancreatic Ductal Cells", Cell Transplant, 4(4):371–383, (1995).

Bonner–Weir et al., "A Second Pathway for Regeneration of Adult Exocrine and Endocrine Pancreas A Possible Recapitulation of Embryonic Development", Diabetes, 42(12):1715–1720, (1993).

Madsen et al., "The Dissociation of Tumor–Induced Weight Loss from Hypoglycemia in a Transplantable Pluripotent Rat Islet Tumor Results in the Segregation of Stable a– and B–Cell Tumor Phenotypes*", Endocrinoloogy, 133(5):2022–2230, (1993).

Pictet and Rutter (1972) in Handbook of Physiology, D. Steiner and N. Frienkel, eds., Williams & Wilkins, Baltimore, MD, pp. 25–66.

(List continued on next page.)

*Primary Examiner*—Leon B. Lankford, Jr.
(74) *Attorney, Agent, or Firm*—Swanson & Bratschun, LLC

(57) ABSTRACT

The subject invention concerns new methods which make it possible, for the first time, to grow functional islet-producing stem cells (IPSCs), islet progenitor cells (IPCs) and IPC-derived islets (IdIs) in in vitro cultures. The subject invention also concerns the use of the in vitro grown IPSCs, IPCs and/or IdIs for implantation into a mammal for in vivo therapy of diabetes. The subject invention further concerns a process of using the implanted cells for growing a pancreas-like structure in vivo that has the same functional, morphological and histological characteristics as those observed in normal pancreatic endocrine tissue. The ability to grow these cells in vitro and pancreas-like structures in vivo opens up important new avenues for research and therapy relating to diabetes.

18 Claims, 12 Drawing Sheets

OTHER PUBLICATIONS

Pontesilli et al. (1987) Clin Exp. Immunol. 70:84–93.
Rao et al. (1990) Cell Differentiation and Development 29:155–163.
Reddy et al. (1988) Diabetologia 31:322–328.
Rosenberg et al. (1992) in Pancreatic Islet Cell Regeneration and Growth, A.I. Vinik, ed., Plenum Press, New York, pp. 95–109.
Shieh et al. (1993) Autoimmunity 15:123–135.
Signore et al. (1989) Diabetologia 32:282–289.
Takaki (1989) In Vitro Cellular and Development Biology 25:763–769.
Teitelman (1993) Tumor Biol. 14:167–173.
Teitelman et al. (1993) Development 118:1031–1039.
Vinik (1992) in Pancreatic Islet Cell Regeneration and Growth, A.I. Vinik, ed., Plenum Press, New York, pp. 1–5.
Wang et al. (1987) Diabetes 36:535–538.
Watanabe et al. (1994) Proc. Natl. Acad. Sci. USA 91:3589–3592.
Wegmann et al. (1993) J. Autoimmunity 6:517–527.
Yu et al. (1990) Tianjin Medical Journal 18:643–647.
Hamashima and Ikehara (1987) in Cellular, Molecular and Genetic Approaches to Immunodiagnosis and Immunotherapy, Kano et al., eds., Karger Pub., pp. 219–226.
Hanafusa et al. (1988) Diabetes 37:204–208.
Hellerstrom et al. (1988) in The Pathology of the Endocrine Pancreas in Diabetes, P.J. Lefebvre and D. G. Pipeleers, eds., Springer–Verlag, Heidelberg, Germany, pp. 141–170.
Jarpe et al. (1990/1991) Regional Immunology 3,305–317.
Kanaka–Gantenbein et al. (1995) Endocrinology 138:3154–3162.
Korsgren et al. (1993) Upsala J. Med. Sci. 98:39–50.
Kuo et al. (1990) Clinical Research 28:58A (Abstract).
Kuo et al. (1992) Pancreas 7:320–325.
McEnvoy and Leung (1982) Endocrinology 111:1568–1575.
Menger et al. (1994) J. Clin. Invest. 93:2280–2285.
Miller et al. (1988) The Journal of Immunology 140:52–58.
Nielson (1985) Acta Endocrinologia, Suppl. 266:7–39.
Otonkoski et al. (1994) Diabetes 43:1164–1166.
Otonkoski et al. (1994) Diabetes 43:947–953.
Peck and Click (1973) European Journal of Immunology 3:385–392.
Peck and Bach (1973) Journal of Immunological Methods 3:147–163.
Altman et al. (1984) Trans. Am. Soc. Artif. Intern. Organs 30:382–386.
Anderson et al. (1993) Autoimmunity 15:113–122.
Baekkeskov et al. (1990) Nature 347:151–156.
Baekkeskov et al. (1982) Nature 298:167–169.
Beattie et al. (1994) J. Clin. Endocrin. Metabol. 78:1232–1240.
Beck–Nielson and Sorenson (1985) Acta Endocrinologica, Suppl. 262:7–9.
Bendelac et al. (1988) The Journal of Immunology 141:2625–2628.
Bendelac et al. (1987) J. Exp. Med. 166:823–832.
Bonner–Weir et al. (1993) Diabetes 42:1715–1720.
Brelje et al. (1994) Diabetes 43:263–273.
Gazdar et al. (1980) Proc. Natl. Acad. Sci. USA 77:3519–3523.
Gu and Saevetnick (1993) Development 118:33–46.
Dialog Biosis Search Results—May 25, 2000.
Dialog WPI Search Results—May 23, 2000.
PubMed Medline Search Results—May 23, 2000 (stem cell and pancreas).
PubMed Medline Search Results—May 24, 2000 (islet and neogenesis).
PubMed Medline Search Results—May 24, 2000 (pancreas and artificial and transplant and beta).

| Product | E | C |
|---|---|---|
| GAPDH | | |
| Insulin-I | | |
| Insulin-II | | |
| Glucagon | | |
| Somatostatin | | |

| Product | C | E |
|---|---|---|
| Reg-I | | |
| Beta/neuroD | | |
| T. Hydroxylase | | |
| IPF-1 | | |
| β-galactosidase | | |

E = IPSCs
C = IdIs

FIG. 9

REVERSAL OF INSULIN-DEPENDENT DIABETES BY ISLET-PRODUCING STEM CELLS, ISLET PROGENITOR CELLS AND ISLET-LIKE STRUCTURES

RELATEDNESS OF THE APPLICATION

This application is a continuation-in-part of copending U.S. Ser. No. 08/547,746, filed Oct. 25, 1995, now U.S. Pat. No. 6,001,647 which is a continuation-in-part of U.S. Ser. No. 08/432,434, filed Apr. 28, 1995, now abandoned, which is a continuation-in-part of U.S. Ser. No. 08/234,071, filed Apr. 28, 1994, now U.S. Pat. No. 5,834,308. Each of the predecessor applications is incorporated herein in its entirety by this reference.

BACKGROUND OF THE INVENTION

Diabetes is a major public health problem. By 1998, 16 million Americans had been diagnosed as having diabetes (American Diabetes Association, 1998).

Ocular complications of diabetes are the leading cause of new cases of legal blindness in people ages 20 to 74 in the United States. The risk for lower extremity amputation is 15 times greater in individuals with diabetes than in individuals without it. Kidney disease is a frequent and serious complication of diabetes. Approximately 30 percent of all new patients in the United States being treated for end-stage renal disease have diabetes. Individuals with diabetes are also at increased risk for periodontal disease. Periodontal infections advance rapidly and lead not only to loss of teeth but also to compromised metabolic function. Women with diabetes risk serious complications of pregnancy. Current statistics suggest that the mortality rates for infants of mothers with diabetes is approximately 7 percent.

Clearly, the economic burden of diabetes is enormous. Each year, patients with diabetes or its complications spend 24 million patient-days in hospitals. Diabetes is our nation's most expensive disease with an estimated total annual cost of $98 billion; however, the full economic impact of this disease is even greater because additional medical expenses often are attributed to the specific complications of diabetes rather than to diabetes itself.

Diabetes is a chronic, complex metabolic disease that results in the inability of the body to properly maintain and use carbohydrates, fats, and proteins. It results from the interaction of various hereditary and environmental factors and is characterized by high blood glucose levels caused by a deficiency in insulin production or an impairment of its utilization. Most cases of diabetes fall into two clinical types: Type I, or juvenile-onset, and Type II, or adult-onset. Type I diabetes is often referred to as Insulin Dependent Diabetes, or IDD. Each type has a different prognosis, treatment, and cause.

Approximately 5 to 10 percent of diabetes patients have IDD. IDD is characterized by a partial or complete inability to produce insulin usually due to destruction of the insulin-producing β cells of the pancreatic islets of Langerhans. Patients with IDD would die without daily insulin injections to control their disease.

Few advancements in resolving the pathogenesis of diabetes were made until the mid-1970s when evidence began to accumulate to suggest that Type I IDD had an autoimmune etiopathogenesis. It is now generally accepted that IDD results from a progressive autoimmune response which selectively destroys the insulin-producing β cells of the pancreatic Islets of Langerhans in individuals who are genetically predisposed. Autoimmunity to the β cell in IDD involves both humoral (Baekkeskov et al., 1982; Baekkeskov et al., 1990; Reddy et al. 1988; Pontesilli et al., 1987) and cell-mediated (Reddy et al. 1988; Pontesilli et al., 1987; Wang et al., 1987) immune mechanisms. Humoral immunity is characterized by the appearance of autoantibodies to β cell membranes (anti-69 kD and islet-cell surface autoantibodies), β cell contents (anti-carboxypeptidase $A_1$, anti-64 kD and/or anti-GAD autoantibody), and/or β cell secretory products (anti-insulin). While serum does not transfer IDD, anti-β cell autoantibody occurs at a very early age, raising the question of an environmental trigger, possibly involving antigenic mimicry. The presence of cell-mediated immunological reactivity in the natural course of IDD is evidenced by an inflammatory lesion within the pancreatic islets, termed insulitis. Insulitis, in which inflammatory/immune cell infiltrates are clearly visible by histology, has been shown to be comprised of numerous cell types, including T and B lymphocytes, monocytes and natural killer cells (Signore et al., 1989; Jarpe et al., 1991). Adoptive transfer experiments using the NOD (non-obese diabetic) mouse as a model of human IDD have firmly established a primary role for auto-aggressive T lymphocytes in the pathogenesis of IDD (Bendelac, et al., 1987; Miller et al., 1988; Hanafusa et al., 1988; Bendelac et al., 1988). Unfortunately, the mechanisms underlying destruction of the pancreatic β cells remain unknown.

Recent efforts to culture pancreatic cells, including efforts reported in the following publications, have focused on cultures of differentiated or partially differentiated cells which in culture have grown in monolayers or as aggregates. By contrast to these reports, the instant invention discloses a method and a structure wherein an islet-like structure is produced which has a morphology and a degree of cellular organization much more akin to a normal islet produced in vivo through neogenesis.

Gazdar, et al. (1980), disclosed a continuous, clonal, insulin- and somatostatin-secreting cell line established from a transplantable rat islet cell tumor. However, the cells disclosed were tumorigenic and were not pluripotent.

Brothers, A. J. (WO 93/00441, 1993), disclosed hormone-secreting cells, including pancreatic cells, maintained in long-term culture. However, the cells cultured are differentiated, as opposed to pluripotent stem cells, which are selected at an early stage for their hormone secreting phenotype, as opposed to their capacity to regenerate a pancreas-like structure.

Korsgren, et al. (1993), disclosed an in vitro screen of compounds for their potential to induce differentiation of fetal porcine pancreatic cells. The instant invention does not depend on the use of fetal tissue.

Nielsen, J. H. (WO 86/01530, 1986), disclosed a method for proliferation of wholly or partially differentiated beta cells. However, this disclosure depended on fetal tissue as a source of the islet cells grown in culture.

McEvoy et al. (1982), disclosed a method for tissue culture of fetal rat islets and compared the effect of serum on the defined medium maintenance, growth and differentiation of A, B, and D cells. Once again, the source of islet cells is fetal tissue.

Zayas et al. (EP 0 363 125, 1990), disclosed a process for proliferation of pancreatic endocrine cells. The process depends on the use of fetal pancreatic tissue, and a synthetic structure, including collagen which is prepared to embed these cells for implantation. The thus produced aggregates of cultured cells upon implantation require 60–90 days before having any effect on blood glucose levels, and require 110–120 days before euglycemia is approached. In contrast, the instant invention provides in vitro grown islet-like structures which do not require collagen or other synthetic means for retention of their organization, and which, upon implantation, provide much more rapid effects on the glycemic state of the recipient.

Coon et al. (WO 94/23572, 1994), disclosed a method for producing an expanded, non-transformed cell culture of pancreatic cells. Aggregated cultured cells are then embedded in a collagen matrix for implantation, with the attendant shortcomings noted for the Zayas et al., EP 0 363 125, structures and the distinctions noted with the structure produced according to the instant invention.

In view of the foregoing reports, the instant invention, wherein functional islet-like structures containing cells which can express insulin, glucagon and/or somatostatin which can be implanted into clinically diabetic mammals which subsequently remain healthy (after elimination of insulin treatment), is surprising. This is because conventional and immunofluorescent histology of the pancreatic islets of Langerhans (Lacey et al, 1957; Baum et al., 1962; Dubois, 1975; Pelletier et al., 1975; Larsson et al., 1975), together with recent three dimensional imaging (Brelje et al., 1989), have revealed a remarkable architecture and cellular organization of pancreatic islets that is ideal for rapid, yet finely controlled, responses to changes in blood glucose levels. It could not be predicted that such a structure could be produced in vitro, particularly when one considers that during embryogenesis, islet development within the pancreas appears to be initiated from undifferentiated precursor cells associated primarily with the pancreatic ductal epithelium (Pictet et al., 1972) i.e. non-islet cells. The ductal epithelium rapidly proliferates, then subsequently differentiates into the various islet-associated cell populations (Hellerstrom, 1984; Weir et al., 1990; Teitelman et al., 1993; Beattie et al., 1994). The resulting islets are organized into spheroid structures in which insulin-producing β cells form a core surrounded by a mantle of non-β cells. For the most part, glucagon-producing α cells (if the islet is derived from the dorsal lobe) or alternatively, pancreatic peptide-producing, PP cells (if the islet is derived from the ventral lobe), reside within the outer cortex (Brelje et al., 1989; Weir et al., 1990). Somatostatin-producing δ cells, which are dendritic in nature, reside within the inner cortex and extend pseudopodia to innervate the α (or PP) cells and the β cells. These spheroid islet structures tend to bud from the ductal epithelium and move short distances into the surrounding exocrine tissue. Angiogenesis-induced vascularization results in direct arteriolar blood flow to mature islets (Bonner-Weir et al., 1982; Teitelman et al., 1988; Menger et al., 1994). Since blood glucose can stimulate β cell proliferation, vascularization may act to increase further the numbers of β cells. Similarly, neurogenesis leads to the innervation of the islets with sympathetic, parasympathetic and peptidergic neurons (Weir et al., 1990). That we have been able to produce functional islet-like structures in vitro which can then be implanted to produce pancreas-like structures, is therefore quite remarkable.

Unfortunately, the cellular organization of the islet can be destroyed in diseases such as type I, insulin dependent diabetes (IDD), in which a progressive humoral and cell-mediated autoimmune response results in specific destruction of the insulin-producing β cells (Eisenbarth, 1986; Leiter et al., 1987). Because the β cell is considered to be, for the most part, a differentiated end-stage cell, it is believed that the body has limited capacity to generate new β cells, thus necessitating regular life-long insulin therapy once the β cell mass is destroyed. However, in experimental animals, the β-cell mass has been shown to increase and decrease in order to maintain euglycemia (Bonner-Weir et al., 1994). This plasticity can occur through two pathways of islet growth: first, by neogenesis, or growth of new islets by differentiation of pancreatic ductal epithelium, and second, by hypertrophy, or expansion through replication of preexisting β cells. During embryogenesis, the β-cell mass initially expands from differentiation of new cells, but by the late fetal stages the differentiated β cells replicate. Replication, then, is likely to be the principal means of expansion after birth, but the capacity to replicate appears to diminish with age. Adult islet cells have been shown to replicate by responding to stimuli known to initiate neonatal islet cell growth, e.g., glucose, growth hormone, and several peptide growth factors (Swenne, 1992; Hellerstrom et al., 1988; Bonner-Weir et al., 1989, Marynissen et al., 1983; Neilsen et al., 1992; Brelje et al., 1993). These observations suggest that the low level of β-cell growth in the adult can accommodate functional demands. For example, during pregnancy or chronic obesity, β cell mass increases significantly yet is reversible since, following termination of pregnancy or after weight loss, an increased β cell death via apoptosis quickly reduces β cell mass.

It is generally accepted that all pancreatic endocrine cell types differentiate from the same ductal epithelium (Pictet et al., 1972; Hellerstrom, 1984; Weir et al., 1990; Teitelman et al., 1993), but whether they are derived from a common stem/precursor cell is uncertain. In normal adult pancreas, approximately 0.01% of the cells within the ductal epithelium will express islet cell hormones and can be stimulated to undergo morphogenic changes to form new islets, reminiscent of neogenesis. This neogenesis has been induced experimentally by dietary treatment with soybean trypsin inhibitors (Weaver et al., 1985), high levels of interferon-γ (Gu et al., 1993), partial pancreatectomy (Bonner-Weir et al., 1993), wrapping of the head of the pancreas in cellophane (Rosenberg et al., 1992), specific growth factors (Otonkoski et al., 1994) and the onset of clinical IDD. Recently, attention has focused on the Reg gene (Watanabe et al., 1994, Otonkoski et al., 1994), identified in a subtracted cDNA library of regenerating rat islets, as a controlling element in the neogenesis of islet β cells. Up-regulation of the Reg gene (e.g., by hepatocyte growth factor/scatter factor) induces β cell proliferation resulting in increased mass, while down-regulation of the Reg gene (e.g., by nicotinamide) induces differentiation of the 'pre-β' cells to mature cells. Thus, a population of precursor/stem cells remain in the adult pancreatic ducts and differentiation of this population can be evoked in vivo in response to specific stimuli. This action may actually occur continuously at low levels.

Although intensive efforts have been made to reproduce islet neogenesis in vitro, minimal success has been achieved. We now describe, for the first time, conditions which permit the growth and expansion of mammalian-derived islet-producing stem cells (IPSCs) in culture, as well as their differentiation to islet-like structures.

Numerous strategies (e.g., bone marrow replacement, immunosuppressive drugs and autoantigen immunizations) have been investigated as possible means to arrest the immunological attack against the pancreatic β cells. However, for these approaches to be effective, individuals who will eventually develop clinical disease must be identified. Most often, patients are identified too late for effective intervention therapy since the immunological attack has progressed to a point where a large percentage of the β cells have already been destroyed. Because the β cell is thought to be an end-stage differentiated cell, it was previously believed that the body has little capacity to regenerate new β cells, thus necessitating regular life-long insulin therapy. Recently, one approach to overcome this problem has been islet cell transplantation. Islet cell transplantation has the disadvantage that the islets are allogeneic which, in turn, can invoke an allo-immune response. Thus, there would be major advantages to growing islets of Langerhans containing functional β cells directly from IDD patients.

Recent observations of the Diabetes Control and Complications Trial (DCCT) that a tight control of glycemia can prevent or significantly reduce the incidence of the long-term complications associated with IDD (The Diabetes Control and Complications Trial Research Group, 1993) have shed light on the importance of the maintenance of the near-normal glucose levels in the periphery and the therapies that will lead to such a strict glycemic control. While intensive insulin therapy that achieves a tight glycemic control demands drastic changes in patient's lifestyle along with increased incidence of hypoglycemic episodes, whole pancreas transplantation is known to render not only a tight glycemic control but also to substantially reduce secondary complications (Fioretto et al., 1998). However, the availability of both allogeneic pancreatic grafts and isolated islets is severely limited by donor availability (Teitelman et al., 1993). Recently, xenogeneic porcine islets have become a promising source of functional β cells, but require encapsulation to avoid autoimmune and xenoreactivities. The encapsulation by itself has not consistently provided protection of xenografts against autoimmune attack in nonobese diabetic (NOD) mouse model (Weber et al., 1997). Further, xenografts pose more serious issue of xenosis (introduction of animal pathogens into humans) (Bach et al., 1998). Thus, there is an urgent need for the development of methodologies to create a reliable and safer source (human) of islets, preferably generated in vitro in large numbers to the meet the demand for transplantation.

BRIEF SUMMARY OF THE INVENTION

The subject invention concerns the discovery that islet-like structures containing insulin-producing β cells, as well as other islet cell types, can be grown in long-term cultures from pluripotent stem cells, i.e., islet producing stem cells or IPSCs. It also has been discovered that IPSCs may give rise to islet progenitor cells, IPCs. IPCs are pluripotent and committed to give rise to islet-like structures containing differentiated α, β, δ and PP cells also found in in vivo islets of Langerhans. Islet-like structures are also referred to herein as IPC-derived islets (IdIs). IdIs contain α (or PP cells), β cells, and optionally δ cells, each of which may be immature, and undifferentiated, proliferating cells.

The novel methods of the subject invention take advantage of the discovery that IPSCs exist even in the pancreas of adult individuals. To obtain IPSCs in vitro, a suspension of pancreatic cells can be cultured in a minimal, high amino acid nutrient medium that is supplemented with normal serum which is preferably derived from the same mammalian species which serves as the origin of the pancreatic cells (homologous serum). Several discrete phases of cell growth result in selection of IPSCs and subsequent progeny which are then induced to differentiate and form IPCs and ultimately IdIs, which are distinguishable from pseudo-islet or pseudo-pancreatic tissue of the prior art. In a first phase, a primary culture of pancreatic cells preferably including ductal epithelium is placed in a low serum, low glucose, high amino-acid basal medium. This culture is then left undisturbed for several weeks to permit establishment of a monolayer of ductal epithelium and to allow the vast majority of differentiated cells to die. Once this ductal epithelium layer is established, cell differentiation can be initiated by re-feeding the cell culture with the high amino acid medium supplemented with homologous normal serum plus glucose. After an additional period of growth, IdIs containing cells which may be immature and/or which may produce insulin, glucagon, somatostatin, pancreatic polypeptide (PP) and/or other endocrine hormones can then be recovered using standard techniques.

It was not previously known or suspected that pancreatic-derived non-islet cells (ductal epithelium) could be used to grow new IdIs, including β cells, in culture. The fortuitous discovery of culture techniques for growing IdIs in vitro eliminates what had previously been a substantial and long-standing barrier to diabetes research. The novel methods and materials described herein enable a better understanding of the mechanisms of diabetes. Furthermore, the ability to produce IdIs from IPSCs in culture now makes certain therapies for diabetes possible for the first time. For example, in accordance with the subject invention, IdIs obtained by culturing pancreatic tissue-derived IPSCs can be implanted in a patient as a way to control or eliminate the patient's need for insulin therapy because the IdIs are able to produce insulin in vivo. The pancreatic tissue can be obtained from the prediabetic or diabetic patient, or from a healthy donor. Thus, the subject invention also concerns the use of the in vitro grown IdIs of the subject invention for implantation into a mammalian species for in vivo treatment of IDD.

The subject invention also greatly facilitates genetic engineering of IPSCs or IPCs to resist subsequent immunological destruction. For example, the cultured IPSCs or IPCs can be transformed to express a protein or peptide which will inhibit or prevent the destructive immune process. Other useful proteins or peptides may be expressed. In addition, expression of specific autoantigens, such as GAD, 64 kD islet cell surface antigens (see Payton et al., 1995), or any other markers identified on the differentiated pancreatic cells, can be eliminated by standard gene knock-out or selection procedures to produce differentiated pancreatic cells which are not or are less susceptible to auto-immune attack. Methods for producing such mutant or knock out cells are well known in the art and include, for example, homologous recombination methods disclosed in U.S. Pat. Nos. 5,286,632; 5,320,962; 5,342,761; and in WO 90/11354; WO 92/03917; WO 93/04169; WO 95/17911, all of which are herein incorporated by reference for this purpose. In addition, a universal donor cell is produced by preparing an IPSC or IPC modified so as not to express human leukocyte antigen (HLA) markers as the cell differentiates into an IdI (see especially WO 95/17911).

Thus, the ability to grow functioning IdIs in vitro from the pancreatic cells of an individual represents a major technical breakthrough and facilitates the use of new strategies for treating and studying IDD. The discovery that IPSCs exist in the adult pancreas circumvents (without excluding) the need to use fetal tissue as a source of cells.

The subject invention also concerns the α, β, δ and PP islet cells produced in vitro according to the methods described herein. These cells are produced from a mammalian pancreatic cell suspension cultured in vitro that gives rise to IdIs which contain the α, β, δ and PP cells which may be immature.

The subject invention further concerns the in vitro growth, propagation and differentiation of IPSCs to generate IPCs, which in turn give rise to the formation of all of the differentiated types of cells that make up normal islets of Langerhans. Moreover, the subject invention concerns the in vivo use of in vitro grown IPSCs, IPCs or IdIs to produce a pancreas-like structure or an ecto-pancreatic structure that exhibits functional, morphological and histological characteristics similar to those observed in the endocrine tissue of a normal pancreas. Thus, a functional ecto-pancreatic structure grown in vivo from implanted ductal epithelium, IPSCs, IPCs and/or IdIs can be used to treat, reverse or cure a wide variety of pancreatic diseases that are known to result in or from damage or destruction of the islets of Langerhans.

BRIEF SUMMARY OF THE FIGURES

In FIG. 6B, the structure has disintegrated, and most of the cells have died, but in FIG. 6C a new structure develops. In FIG. 6D, several new IdIs have formed. This series of serial passage steps can be repeated a number of times until the IPSCs become depleted. In this event as the IdI disintegrates, as in FIG. 6E, instead of new IdIs being formed, the differentiated cells multiply, as shown in FIG. 6F. It is this type of proliferated differentiated cell that is thought to have been produced by workers such as Coon et al. (see WO 94/23572).

FIG. 9 is a RT-PCR profile of mRNA transcripts for GAPDH, insulin-I, insulin-II, glucagon, somatostatin, Reg-I, β/neuroD, tyrosine hydroxylase, IPF-1 and β-galactosidase in IPSCs and in IdIs.

ABBREVIATIONS AND DEFINITIONS

IPSCs are Islet Producing Stem Cells. IPSCs are a small population of cells derived from ductal epithelium (i.e., pancreas-derived) discovered in fetal or adult pancreas which, according to this invention, have the capacity of giving rise in vitro to IPSC undifferentiated progeny or to islet progenitor cells (IPCs), which in turn give rise to islet-like structures or IPC-derived islets (IdIs). IPSCs may also give rise to exocrine tissue, including acinar cells. IPCs are pluripotent and committed to give rise to the differentiated cells of the in vivo islets of Langerhans and the IdIs.

Figure 3A:
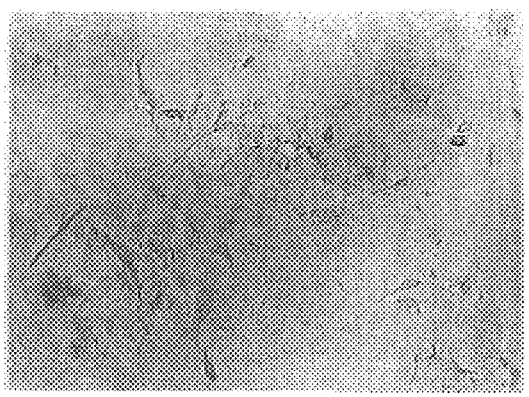
FIGS. 3A through 3H shows sequential stages in the development of an IdI in vitro from 3A, which shows a few cells after several weeks in culture, which have survived and which begin to bud (FIG. 3B, dark structure in top right-hand of field), and divide (FIG. 3C several locations in field), and to form highly organized structures (FIGS. 3D–3H) under the culture conditions described herein.
Figure 3B:
Figure 3C:
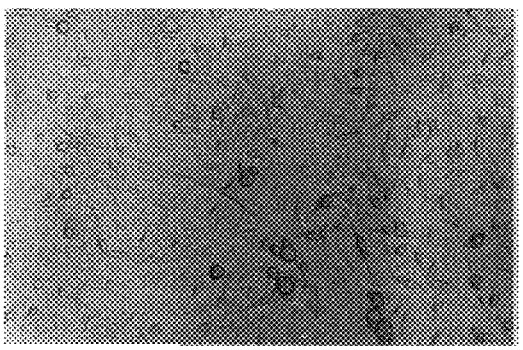
Figure 3D:
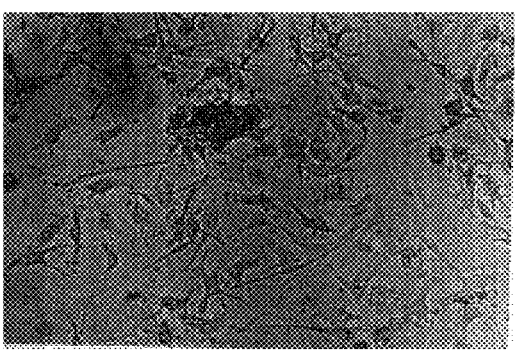
Figure 3E:
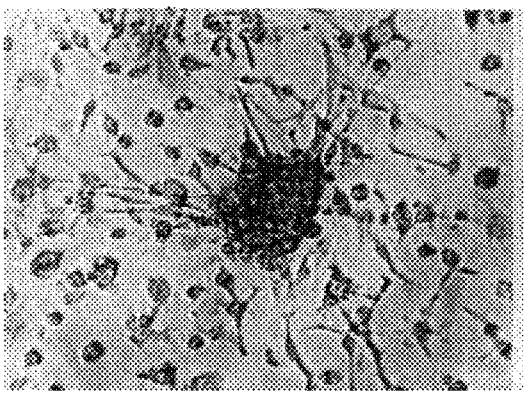
Figure 3F:
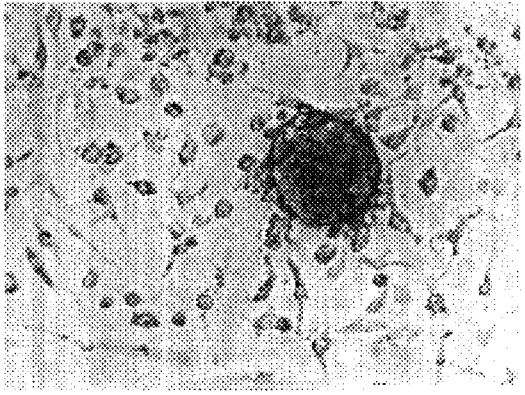
Figure 3G:
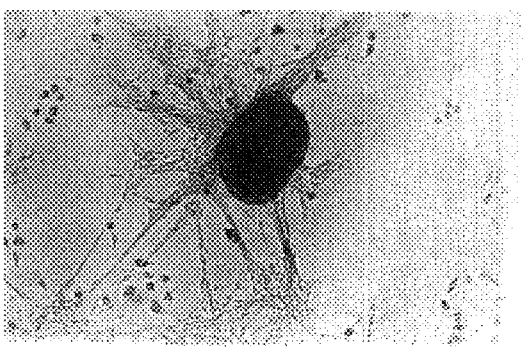
Figure 3H:
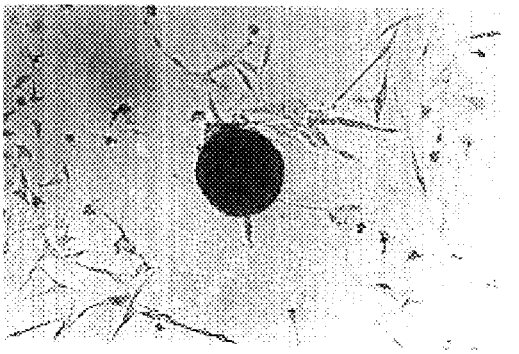
Figure 4A:
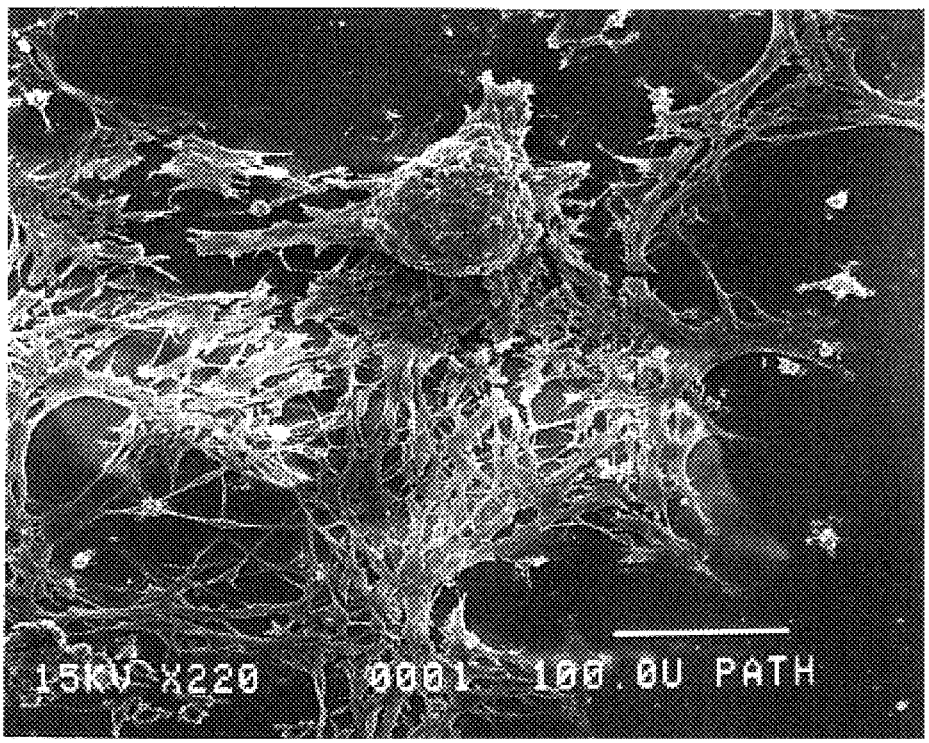
FIG. 4 shows photomicrographs of the structures shown in FIGS. 3G–3H, showing the highly organized morphology thereof.
Figure 4B:
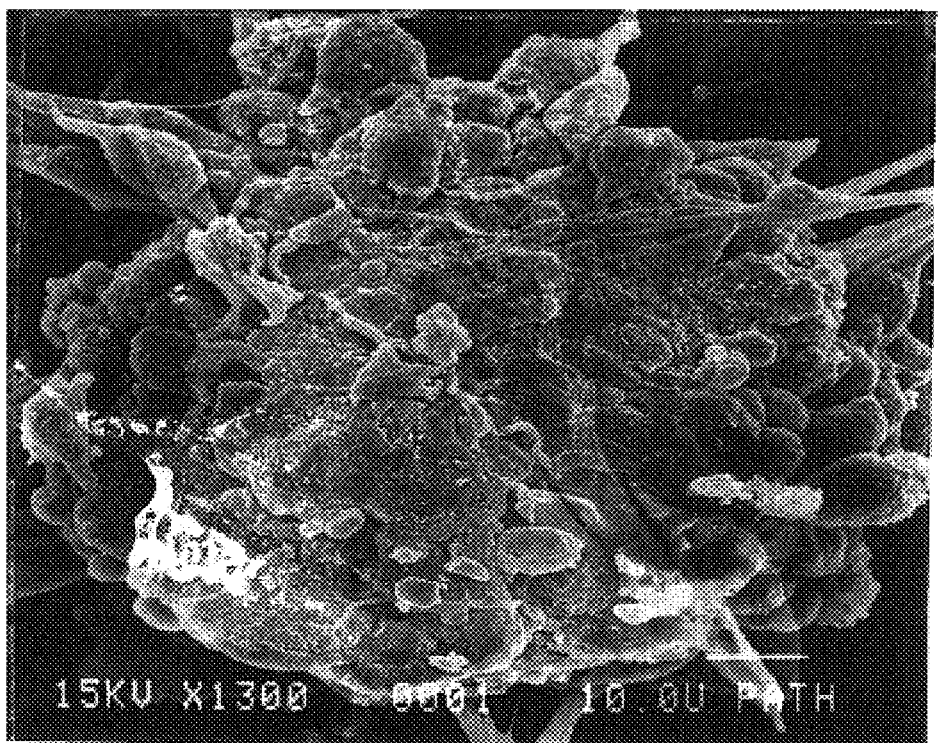
Figure 5:
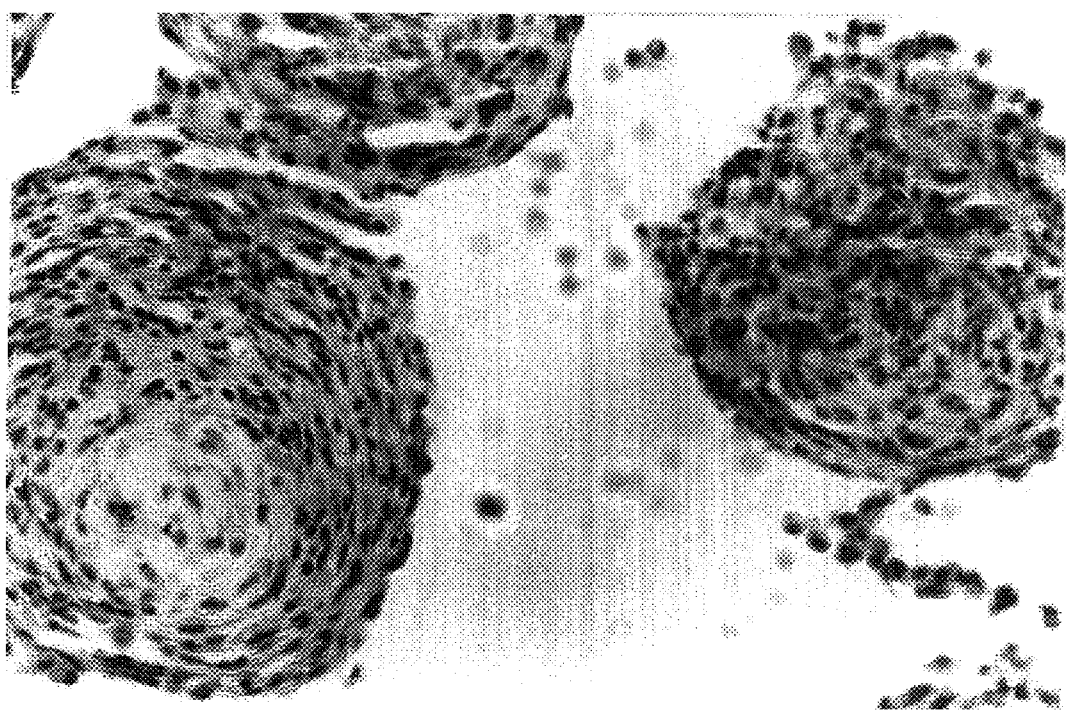
FIG. 5 shows H/E staining of an IdI cross-sections showing the highly organized morphology of the structure with β-cells in the center and glucagon-producing cells at the periphery.

Islet-like structures or IPC-derived islets (IdIs) are highly-organized structures of cells which we have discovered arise in culture indirectly from IPSCs (see FIG. 3H, FIGS. 4A and 4B, and cross-section shown in FIG. 5). IdIs in vitro typically have α (or PP) and β cells, and optionally may have δ cells, depending on the state of maturation of the IdI. Implantation of early or immature Idis can induce in vivo maturation of each cell type. IdIs have a characteristic ratio of α or PP cells to β cells and have an enhanced response to glucose challenge relative to ex vivo adult islets. In IdIs, about 20–25% of cells are β cells containing basal levels of insulin and glucagon, as compared to about 60% in adult in vivo islets. IdIs are also less subject to autoimmune attack upon implantation relative to islets produced by other culture methods.

Islet cells are cells found in in vivo islets of Langerhans or in Idis. They can include the differentiated or immature α, β, δ and PP cells, and the predecessor IPCs. IdIs and islets may also contain IPSCs, or it may be the case that IPCs dedifferentiate to IPSCs under culture conditions described herein.

A pancreas-like structure is the tissue that results from the in vivo implantation of IdIs, ductal epithelium, IPSCs, IPCs or any combination thereof. A pancreas-like structure contains endocrine tissue, preferably in the form of IdIs containing β and α or PP cells, and optionally δ cells. The IdIs in the pancreas-like structure may contain partially differentiated or fully mature β, δ and α or PP cells. The pancreas-like structure may consist entirely of the originally implanted cells, and/or may contain progeny of the originally implanted cells. The pancreas-like structure is preferably vascularized. The pancreas-like structure preferably does not contain acinar cells and exocrine tissue. The term pancreas-like structure is not intended to be synonymous with pancreas. A pancreas-like structure is substantially composed of endocrine tissue (i.e., at least 50%, and preferably at least 75%, 90% or 95% by weight). In contrast, a pancreas contains only 1–3% endocrine tissue. When the pancreas-like structure is located at a site other than the natural pancreatic location in vivo, the pancreas-like structure is referred to as an ecto-pancreatic structure. Sites of implantation include in the natural pancreas, under the kidney capsule or in a subcutaneous pocket. It is particularly important that an ecto-pancreatic structure contain substantially no exocrine tissue as overproduction of pancreatic enzymes can be harmful to the health of the recipient.

DETAILED DESCRIPTION OF THE INVENTION

According to the subject invention, Idis can for the first time be grown in in vitro cultures. The techniques of the subject invention result in cell cultures which can produce insulin, glucagon, somatostatin, PP and other endocrine hormones. Other useful proteins may also be produced by, for example, transforming the IPSC or IPC with DNA which encodes proteins of interest. The ability to grow these functional cell cultures enables those skilled in the art to carry out procedures which were not previously possible. In the following disclosure, the term IdI refers to IPC-derived islet-like structures that have most of the attributes of islets of Langerhans produced in vivo during normal neogenesis. The immature nature of these structures permits implantation in vivo with rapid final differentiation and vascularization ensuing to provide a functioning replacement to damaged or otherwise compromised islets of Langerhans in recipients such as diabetic or prediabetic mammals, in need of such treatment.

The method of the subject invention involves making suspensions of cells, including ductal epithelium that contains stem cells (IPSCs), from the pancreas of a mammal. Preferably, the cells would be from the pancreas of a healthy or prediabetic mammal. However, it is also contemplated that pancreatic cells from mammals already showing clinical signs of diabetes, can be utilized with the subject invention. The cell suspensions are prepared using standard techniques. The cell suspension is then cultured in a nutrient medium that facilitates the growth of the ductal epithelium and subsequent IPSCs, while at the same time severely compromising the sustained growth of the differentiated or mature cells. In a preferred embodiment, the nutrient medium is one which has a high concentration of amino acids. One such medium is known as Click's EHAA medium and is well known and readily available to those skilled in the art (Peck and Bach, 1973, herein incorporated by reference for this purpose). Other equivalent nutrient media could be prepared and utilized by those skilled in the art. What is required for such media is that they have little or no glucose (less than about 1 mM) and low serum (less than about 0.5%). The high amino acid concentrations are preferably of amino acids known to be essential for the cells of the species being cultured, and provide a carbon source for the cultured cells. In addition, at least one rudimentary lipid precursor, preferably pyruvate, is provided. These conditions are so stressful to most differentiated cell types that they do not survive. Surprisingly, however, upon extended culture of cells from pancreatic tissue without re-feeding (about 3 weeks) IPSCs and/or ductal epithelial cells do survive and after extended culture, begin to proliferate. Subsequent culture phases employ media supplemented with normal serum from the same species of mammal from which the pancreatic cells originate. Thus, in the case of mouse cells, the medium is supplemented with normal mouse serum, whereas in the case of human cells the medium is supplemented with normal human serum. The preparation of normal serum is well known to those skilled in the art. The concentration of normal serum used with the cell culture method of the subject invention can range from about 0.5% to about 10%, but for mice is preferably about 1%. For human serum, a higher concentration is preferred, for example, about 5%.

The cell suspension prepared in the nutrient medium supplemented with normal serum and about 2.5–10 mM glucose is then incubated under conditions that facilitate cell growth, preferably at about 37° C. and, preferably, in an atmosphere of about 5% $CO_2$. This incubation period is, thus, carried out utilizing standard procedures well known to those skilled in the art. During this time ductal epithelial cells proliferate and establish a monolayer which will ultimately give rise to IPSCs. The initiation of cellular differentiation can be brought about by re-feeding the cultures with Click's EHAA or like medium supplemented with normal serum as discussed above. Rapid re-feeding was found to induce extensive IPC and IdI formation with considerable cell differentiation. We have found that cellular differentiation is further enhanced by inclusion of relatively high concentrations of glucose (about 10–25 mM and preferably 16.7 mM) in the re-feed medium. In addition, it is contemplated that any of a number of other biological factors, including but not limited to factors which up-regulate the Reg gene, such as hepatocyte growth/scatter factor, and other cellular growth factors, such as insulin-like-growth factor, epidermal growth factor, keratinocyte growth factor, fibroblast growth factor, nicotinamide, and other factors which modulate cellular growth and differentiation can be added to the cultures to optimize and control growth and differentiation of the IPSCs. By employing any of these various factors, or combinations thereof, at different stages, at different seeding densities and at different times from seeding in the course of IPSC differentiation, IPSC cultures are optimized. In addition, factors produced by the IPSC cultures in the course of differentiation which augment growth can be isolated, sequenced, cloned, produced in mass quantities, and added to IPSC cultures to facilitate growth and differentiation of those cultures. The relevant factors are identified by concentrating IPSC culture supernates from early, intermediate and late stages of differentiation and testing for the ability of these concentrates to augment IPSC growth and differentiation. Positive effects are correlated with molecular constituents in the concentrates by two-dimensional gel electrophoresis of positive and negative supernates, purification and N-terminal sequencing of spots present only in the positive concentrates and subsequent cloning and expression of the genes encoding these factors.

Upon histological examination of the cells in the IdIs, at least three distinct cell types were identifiable and appeared similar to islet cells prepared from islets of control mice. The time required for IPSC differentiation to occur decreased as the frequency of re-feeding following the initial three week period was increased.

We have been able to propagate and expand IdI-producing cultures through the serial transfer of ductal epithelium plus islet foci (aggregates of IPSCs and IPCs where IdI growth has been initiated) to new culture flasks. In less preferred, less efficient embodiments, only IdIs or IPSCs need be serially transferred. These embodiments are less preferred as more time is required for the development of new IdI-containing cultures. Any of these serial transfer embodiments can generate sufficient numbers of IdIs for use in methods described herein, for example, for reversing the metabolic problems of IDD.

In order to determine whether the IdIs produced in vitro according to the subject invention could reverse IDD, the IdIs were implanted into NOD mice. Mice that received the implants exhibited a reversal of insulin-dependent diabetes, whereas untreated NOD mice showed signs of progressive clinical disease. In addition, no autoimmune pathogenesis was observed for the three months of observation that followed implantation. Thus, the IdI implants of the subject invention can be used in vivo to treat diabetes in mammals, including humans.

In a preferred embodiment of the subject invention, the progression of diabetes can be slowed or halted by re-implantation of autologous islets engineered to be resistant to specific factors involved in the immunological attack. For example, the IPSCs, IPCs, or cells of the IdIs can be engineered so that they are resistant to cytotoxic T cells (see, for example, Durinovic et al., 1994, identifying islet specific T-cells and T-cell receptor sequences which are similar to insulitis-inducing T-cells of diabetic mice; Elias and Cohen, 1994, identifying peptide sequences useful in diabetes therapy in NOD mice by turning-off production of specific diabetogenic T-cell clones; Conrad et al., 1994, describing a membrane-bound, islet cells superantigen which triggers proliferation of islet infiltrating T-cells; Santamaria et al., 1994, describing the requirement of co-expression of B7-1 and TNFα for diabetes and islet cell destruction; any of these antigens may be eliminated according to known methods to improve the resistance of the implanted cells against immunologic attack). The availability of long-term cultures of IdIs can also be used in investigations into the pathogenesis of IDD, including the cellular recognition of β cells, the mode of islet infiltration, and the immune mechanisms of β cell destruction. Furthermore, this technology facilitates transplantation of autologous IdIs. The growth of IdIs according to the procedures of the subject invention has great utility in teaching students and in increasing the understanding of important aspects relating to cell differentiation and function.

In a further embodiment of the subject invention, IPSCs have been grown in vitro from pancreas cells isolated from a mammal. A surprising discovery using these in vitro grown cells in conjunction with the methods of the subject invention, was the ability to establish and/or grow and produce, in vivo, a pancreas-like structure that exhibited functional, morphological and histological features and characteristics similar to the endocrine tissue of a normal pancreas. The pancreas-like structure produced in vivo according to the subject invention, represents a major scientific discovery and provides a novel means for studying, treating, reversing or curing a number of pancreas-associated pathogenic conditions including but not limited to pancreatitis, pancreatic cancer and IDD. This is accomplished by removal of the diseased tissue and implantation of the cells produced according to this invention. A pancreas-like structure can be produced by implantation of ductal epithelium, IPSCs, IPCs, IdIs or any combination thereof. Preferably, both ductal epithelium (containing IPSCs) and IdIs are transplanted.

Because this invention provides a method for culturing IPSCs and producing Idis in vitro, study of the growth and differentiation of IPSCs is now possible. Accordingly, all of the known methods of cell culture, purification, isolation and analysis can be brought to bear on the significant questions regarding how many types of cells are involved in pancreatic cell differentiation. These methods include, but are not limited to, fluorescence activated cell sorting (FACS), magnetic bead usage (as in, for example, the use of the commercially available DYNA BEADS™ which are specifically adapted for this purpose), use of magnetically stabilized fluidized beds (MSFB, see U.S. Pat. No. 5,409,813), and any of a number of other methods known in the art. The pathway for this process is now amenable to dissection. Markers (including cell-surface, intracellular, protein or mRNA), specific to every stage of this process, are also now readily identifiable and capable of being manipulated through application of standard techniques including, but not limited to: production of antibodies, including monoclonal antibodies, to cells, cell surface markers, and cellular components which differ throughout the process of pancreatic IPSC differentiation; production of T-lymphocytes which specifically respond to antigens expressed by the pancreatic cells at different stages in the maturation and differentiation process (see, for example, Wegmann et al., 1993); identification and elimination of cell surface markers recognized by T-cells and which, therefore, result in differentiated β-cell destruction if present (see references above); identification of factors significant in bringing about the different stages of maturation and the different factors produced by the differentiating cells; subtractive hybridization of nucleic acids isolated from cells at different stages in the maturation process, enabling pinpointing of gene products significant to each aspect of the cellular differentiation; differentiated display PCR (see Liang et al., 1992); arbitrarily primed PCR (see Welsh et al., 1992); and representational difference analysis PCR (RDA-PCR) (see Lisitsyn, 1993).

Additionally, standard methods can be applied to enhance the success of implantation including: encapsulation of single IPSCs, IPCs, IdIs or populations thereof for implantation in appropriate host organisms, thereby providing advantages that such methods have demonstrated in implantation of other types of progenitor or engineered cells (see Altman et al., 1994); genetic engineering of the IPSCs or IPCs to produce cells less susceptible to autoimmune attack, such as by knock-out of autoantigen genes, or insertion of resistance enhancing genes; insertion of other genes including those which provide altered cellular surface antigens or which provide different biochemical properties to the internal milieu of the cells including genes which express enzymes which increase or decrease the sensitivity of the cells to glucose or genes which increase or decrease the responsiveness of the cells to growth factors or improve resistance to autoimmune attack; and insertion of genes which increase or decrease the production of insulin, glucagon or somatostatin. Examples of how these types of modifications can be introduced into the IPSCs and IPCs include electroporation, virus vectors, transfection or any of a number of other methods well known in the art (see for example WO 95/17911; WO 93/04169; WO 92/03917; WO 90/11354; U.S. Pat. No. 5,286,632; WO 93/22443; WO 94/12650; or WO 93/09222; all of which are incorporated by reference for this purpose). Production of universal donor (knock-out) cells which, for example, have deleted or otherwise modified human leukocyte antigens is illustrated in WO 95/17911. Because this process does not depend on the use of fetal tissue, it is possible to remove pancreatic tissue from a mammal suffering from IDD or at risk of suffering from IDD, or from a healthy mammal, grow IdIs in vitro and implant those structures into the individual to produce physiologically relevant amounts of insulin in response to fluctuations in blood glucose.

It will also be recognized that data presented herein reveal that in vitro neogenesis of IdIs from pancreatic cells is possible, but involves several distinct phases of growth, including: 1) establishment of a stromal, or nurse, cell monolayer of ductal epithelial cells which permits the generation of IPSCs; 2) induction of IPSC proliferation with specific culture conditions which promote cyclical regeneration of IPSCs and also prevent premature differentiation of the IPSC; 3) differentiation of IPSCs to form IPCs and IdIs comprising α, β and optionally δ cells. The composition of the IdIs is dictated by the culture environment, as differences in culture nutrients and growth factors result in IdIs containing different percentages of the various differentiated islet cell types. Identification of in vitro conditions which induce the β cell to its final maturation stage, i.e., formation of insulin-containing granules and glucose responsiveness can also now be achieved. A factor present in vivo which achieves this final differentiation is identified by addition of cellular extracts or growth factors to the IPSC cultures.

We have maintained primary IPSC cultures for up to 10 months and secondary cultures an additional 14–16 months, with each capable of expansion and differentiation to form IdIs. While the ability to grow IdIs from healthy or prediabetic adults represents a major technical breakthrough and focuses attention on possible new strategies for attaining a cure for IDD, perhaps the most important aspect of this work is the demonstration that IPSCs and IPCs exist in the islets of both normal and prediabetic adults. This finding will eliminate the need to use either fetal, allogeneic or xenogeneic tissue for transplantation of β cells into IDD patients; and will promote the development of novel strategies to reverse hypoglycemia in vivo. It will also permit the study immunological responses to newly implanted IdIs; and/or will create IdIs resistant to immunological attack.

It is tempting to speculate, based on the data presented herein, that the well-documented period of remission in type I IDD patients following onset of disease might actually represent a time when IPSC and/or IPC growth is induced, only to be subsequently overwhelmed by the on-going autoimmune reaction. Since implantation of autologous islets has been thought in the art to require cells engineered to be resistant to the immunological attack, identification and culture of IPSCs and IPCs as disclosed herein is essential for the genetic engineering efforts described above.

Surprisingly, the in vitro-generated IdI implants of this invention showed no signs of immunological attack over the time period studied (3 months). It is possible that the autoantigen(s) are not expressed on cultured cells, or that the autoantigen(s) cannot be presented since culture dilutes out the macrophages, or such implants may induce peripheral tolerance. The availability of long-term cultures of IdIs facilitates investigations into the pathogenesis of IDD, including the cellular recognition of β cells, the mode of islet infiltration, and the immune mechanisms of β cell destruction. Furthermore, this technology facilitates IdI transplantation, autologous islet replacement with self-IdIs, and reduction in the need for insulin therapy.

Accordingly, this invention provides a method for the in vitro growth of IPSCs to produce IdIs. The method comprises culturing pancreatic cells from a mammalian species in a basal nutrient medium supplemented with normal serum at below about 0.5% and glucose at below about 1 mM, allowing the IPSCs to grow for at least 3 weeks, and initiating cellular differentiation into mature islet cells by re-feeding the IPSCs in culture with a nutrient medium supplemented with normal serum at about 0.5–10% and glucose at about 2.5 mM–10 mM. The pancreatic cells may be from any mammal, including humans and mice, and the serum is from the same species. The medium preferably contains all of the amino acids essential to growth of cells from the species being cultured and in such quantity as to ensure that the culture does not become depleted. Upon re-feeding, the re-feed medium preferably contains glucose and serum in sufficient quantities to stimulate differentiation. Furthermore, according to this method, once differentiation has begun, the cells are preferably re-fed frequently (about once per week).

This method also provides a source of endocrine hormones, including but not limited to insulin, and possibly glucagon, PP and somatostatin, which may be recovered from the culture medium or which can be directly released into a mammal by implantation of the IdIs, IPSCs, IPCs and/or ductal epithelium into the tissue of a mammal to produce a pancreas-like structure. Such implantation provides a method for treating pancreatic disease in a mammal by implanting said cells or tissues to produce a pancreas-like structure in the mammal. In one embodiment, the IPSCs, IPCs or IdIs of this invention are genetically modified so as to not produce IDD autoantigens or HLA markers such that they do not express insulin dependent diabetes associated autoantigens, other than insulin, or which have been modified so that they do not express HLA antigens, as said IPSCs or IPCs differentiate into said pancreas-like structure. Furthermore, the ductal epithelium, IPSCs, IPCs and/or IdIs may be encapsulated in an insulin, glucagon, somatostatin and other pancreas produced factor permeable capsule. The appropriate implantation dosage in humans can be determined from existing information relating to ex vivo islet transplantation in humans, further in vitro and animal experiments, and from human clinical trials. From data relating to transplantation of ex vivo islets in humans, it is expected that about 8,000–12,000 IdIs per patient kg may be required. Assuming long-term survival of the implants following transplantation (e.g., in the case of encapsulation or genetic engineering), less than the number of naturally occurring islets (about 2 million in a normal human adult pancreas), or possibly even less than the amount used in ex vivo islet transplantation may be necessary. From in vitro culture and in vivo animal experiments, the amount of hormones produced can be quantitated, and this information is also useful in calculating an appropriate dosage of implanted material. Additionally, the patient can be monitored to determine adherence to normoglycemia. If such testing indicates an insufficient response or hyperinsulinemia, additional implantations can be made or implanted material reduced accordingly.

Also provided is a method for analyzing the differentiation of IPSCs which comprises culturing at least one IPSC in vitro, and inducing said IPSC to begin differentiation into a pancreas-like structure. This method also permits identification of mRNA or protein markers specific to a plurality of different stages in the differentiation process. The protein markers may be expressed on the cell-surface, be secreted, or they may be intracellular. In another aspect of this invention a ligand binding molecule and a method for making a ligand-binding molecule which selectively binds to IPSCs, IPCs, or to more differentiated pancreatic cells is provided. Ligand binding molecules include monoclonal and polyclonal antibodies and nucleic acid ligands (e.g., U.S. Pat. No. 5,270,163). The method of obtaining monoclonal antibodies comprises the fusion of B-lymphocytes from IPSC immunized animals (e.g., rats) with myeloma cells, and culturing and expanding the myelomas to obtain antibodies. These ligand-binding molecules (e.g., antibodies or nucleic acid ligands) thus provide a method of isolating IPSCs, IPCs or other differentiated pancreatic cells at any stage between that of IPSC and a fully differentiated pancreatic cell. This method comprises selecting the target cell from a population of cells comprising the target cell, with a specific ligand-binding molecule which binds to a protein marker expressed by the target cell at a given stage of differentiation. Alternatively, the method comprises selecting and removing other cells from a population of cells comprising the target cell with a specific ligand binding molecule which binds to a protein marker absent on the surface of the target cell.

In yet another aspect, this invention provides a method for treating a mammal suffering from, or at risk of developing IDD, which comprises:

a. removing pancreatic tissue from the mammal;
b. culturing IPSCs and ductal epithelium present in the pancreatic tissue in vitro to generate IPSCs, IPCs and/or Idis; and
c. implanting said ductal epithelium, IPSCs, IPCs and/or IdIs into said mammal.

In a further aspect of this invention, there is provided an IPSC modified so as not to express insulin dependent diabetes autoantigens in either the undifferentiated or in the differentiated state of the IPSC. Preferably, the autoantigen which is not expressed as a result of the modification is selected from GAD, 64 kD islet cell antigen, and HLA markers.

As part of the method of this invention, a method for in vitro neogenesis of IdIs from IPSCs is provided which comprises:

a. establishing a stromal, or nurse, cell monolayer of ductal pancreatic epithelial cells which includes IPSCs;

b. inducing IPSC proliferation with culture conditions which promote cyclical regeneration of IPSCs and also prevent premature differentiation of the IPSCs; and c. expanding and differentiating the IPSCs to produce IPCs which give rise to IdIs comprising α and β cells, proliferating, undifferentiated cells, and possibly δ cells. Preferably, the culture-generated IdI is characterized by large, differentiated cells which stain with insulin-specific stain in the center of the IdI; small differentiated cells which stain with glucagon-specific stain at the periphery; and proliferating and undifferentiated cells which do not stain with any of the endocrine hormone-specific stains in the inner cortex. The structure is further characterized in that, upon breaking the structure into single cell suspensions by mechanical or other means in the presence of a proteolytic enzyme and subsequent staining of individual cells, individual cell populations which stain either with glucagon-specific stain (α cells), insulin-specific stain (β cells) or somatostatin-specific stain (δ cells) are observed.

The method of in vitro neogenesis of islets according to this invention preferably comprises:

a. dispersing and leaving undisturbed pancreatic cells in a minimal culture medium comprising little or no glucose, serum at a concentration below about 0.5%, essential amino acids for the cells of the species from which the pancreatic cells were obtained, and a lipid source, until about 99% of the cells in said culture have died (phase I);

b. re-feeding the culture of step (a) with the minimal medium supplemented with about 1–10 mM glucose and about 0.5%–10% serum (but less than a toxic amount) and re-feeding about once a week until rapid proliferation occurs;

c. re-feeding the culture of step (b) with the minimal medium supplemented with 0.5%–10% serum and about 10–25 mM glucose and, optionally, added growth or cellular factors (phase III);

d. allowing IdIs to bud into the medium;

e. recovering the IdIs.

This process may be repeated several times by serially transferring ductal epithelium (or IPSCs) plus early-stage, proliferating IdIs in culture in vitro.

As used herein, the term "growth" refers to the maintenance of the cells in a living state, and may include, but is not limited to, the propagation and/or differentiation of the cells. The term "propagation" refers to an increase in the number of cells present in a culture as a result of cell division.

Following are examples which illustrate procedures, including the best mode, for practicing the invention. These examples should not be construed as limiting. All percentages are by weight and all solvent mixture proportions are by volume unless otherwise noted.

EXAMPLE 1
Culturing of Functional Islets of Langerhans

Figure 1A:
FIGS. 1A through 1D show cells grown according to the procedures of the subject invention.

Single cell suspensions of islet cells were prepared from whole islets isolated from the pancreas of 19–20 week old prediabetic male NOD/UF mice, as detailed elsewhere (Shieh et al., 1993). Typically, about 25% of the male mice in a NOD colony will have overt IDD at this age and all will have severe insulitis. The islet cells were resuspended in glucose depleted or glucose-free Click's EHAA medium (Peck and Bach, 1973; Peck and Click, 1973) supplemented with normal mouse serum (NMS) to 0.25%, plated in a 25 $cm^2$ tissue culture flask, and incubated at 37° C. in a 5% $CO_2$ atmosphere. At this stage, two outcomes are possible: first, the islet-infiltrating cells may dominate, thus permitting the establishment of immune cell lines, or second, ductal epithelial cells (often referred to as stromal cells in these cultures) may dominate, thus allowing the growth of a nurse cell monolayer. Growth of ductal epithelial monolayers appeared to result when islet-infiltrating cells were plated simultaneously but in limited numbers. Enrichment of the islet cells with decreased numbers of infiltrating cells can be achieved by gradient separation (Jarpe et al., 1991). The vast majority (>99%) of the original cells die during this incubation period, leaving a small number of epithelial-like cells attached to the culture dish (FIGS. 1A and 3A, Stage I). Epithelial cell cultures, when left undisturbed for 4–5 weeks (i.e., no re-feeding) proliferated to cover the entire bottom surface of the culture vessel (FIGS. 3C and 3D).

Figure 1B:
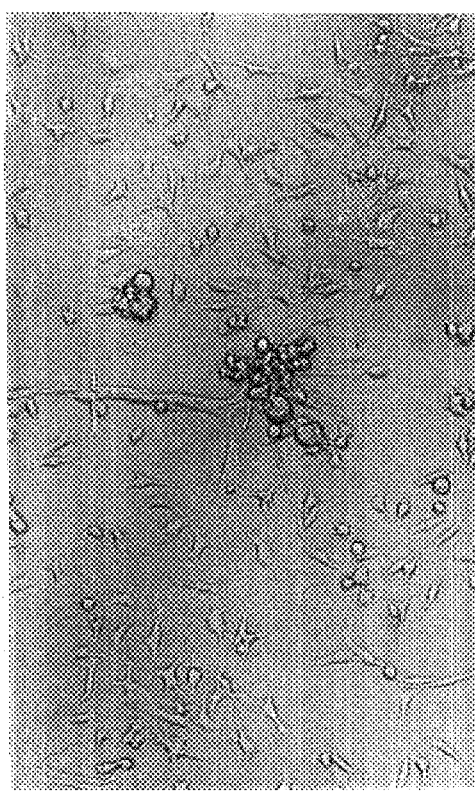

Differentiation and endocrine hormone expression of the cultures was initiated by re-feeding the cultures with Click's EHAA medium supplemented with NMS and a sugar solution comprising glucose or sucrose or other sugar equivalents. Typically, the sugar is glucose. The concentration of glucose can be between about 0.25 mM to about 10 mM, but typically is about 2.5 mM. Normal NOD or NMS serum at about 0.5% is also preferably included. Techniques for re-feeding cell cultures in vitro are well known in the art and typically involve removing from about 50% to about 90% of the old nutrient medium and adding fresh medium to the culture flask. Rapid re-feeding induced the formation of increasing numbers of centers of IPSC, IPC and IdI growth (referred to herein as foci) exhibiting cell differentiation. The rate of re-feeding can be, for example, at about one week intervals. Preferably, the rate of re-feeding is at about 5 to 6 day intervals. Small rounded cells (IPSCs or IPCs) appeared on top of the epithelial monolayers, almost as if by budding (FIGS. 1B and 3D, Stage II).

Figure 1C:
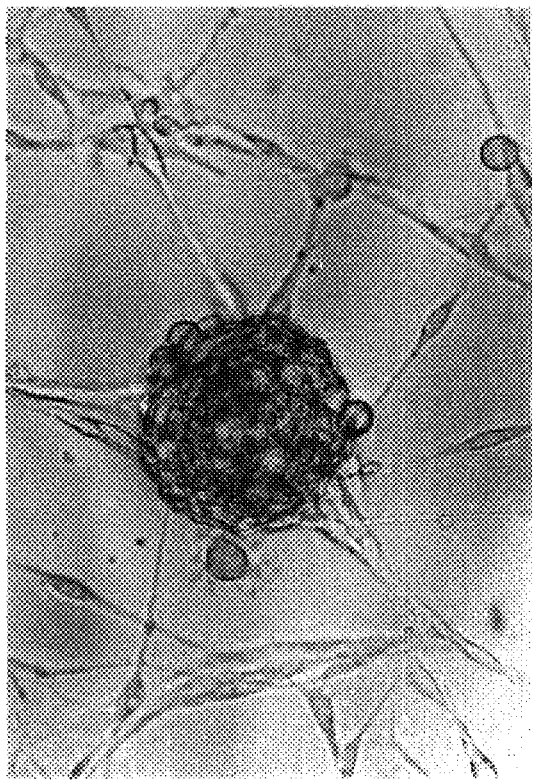
Figure 2:
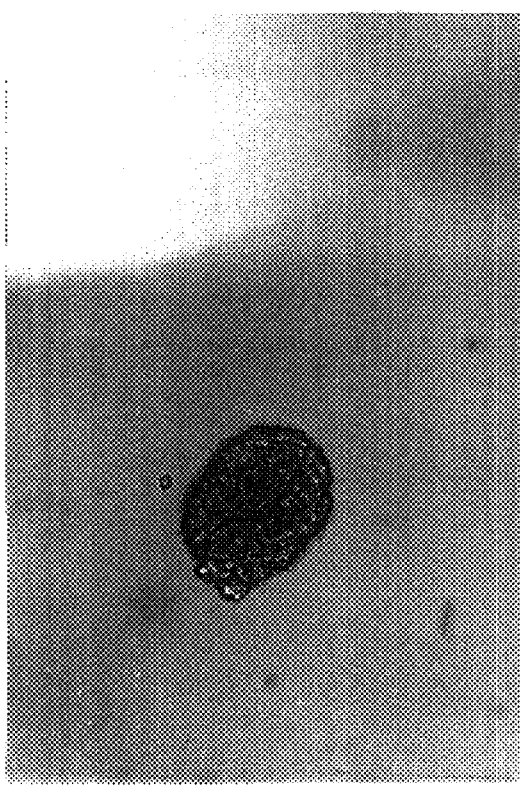
FIG. 2 shows an IdI grown according to the subject invention.
Figure 1D:
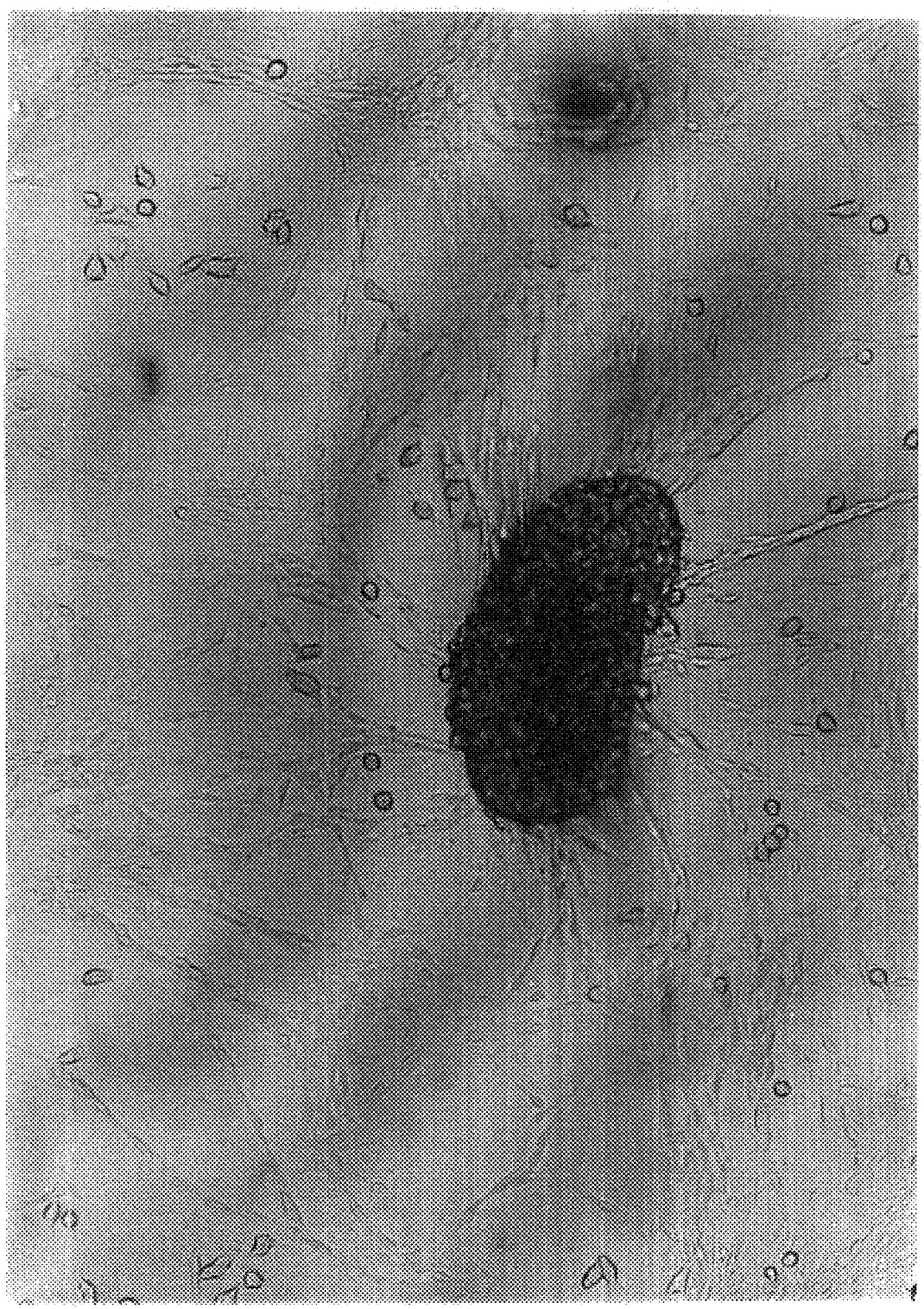

At peak production, as many as 50–100 foci occurred simultaneously in a single 25 $cm^2$ (4 $in^2$) tissue culture flask. Each individual rounded cell underwent rapid proliferation, with the daughter cells forming foci (FIG. 1C). Rapid re-feeding induced increasing numbers of foci as well as increased numbers of cells within each foci. Induction of IdIs (Stage III) was enhanced through re-feeding of cultures with EHAA medium supplemented with normal mouse serum (0.5%) and high levels of glucose (10 mM-25 mM and preferably about 16.7 mM glucose—See FIGS. 1D and 3E–3F). As the cell proliferation and differentiation proceeded, the organization of the IdI took place and the IdI even appeared to surround itself with a capsular material. IdIs (Stage IV) appeared as smooth spheroids composed of tightly clustered cells (FIGS. 3F–3H). This differentiation appears to be enhanced when serum from NOD mice is used rather than serum from other strains of mice, and higher levels of insulin-like growth factor (IGF), epidermal growth factor (EGF) and/or hepatocyte growth factor (HGF) in the NOD mouse serum are believed to be responsible for this effect. The IdIs generally grew to a constant size (about 100–15 Å, FIG. 2, although fusion of two IdIs resulted in IdIs about twice the general size), then detached off of the epithelial layers to float in the medium. These free-floating IdIs tended to break down within 48–72 hours, similar to what is observed when pancreatic islets are isolated from in vivo sources and then cultured under similar conditions. Serial rounds of this process may then be conducted (see FIGS. 6A–6D and Example 5 below).

The IdIs, collected after natural detachment or removal from the epithelial layers using a Pasteur pipette, were gently washed in medium, then broken into single cell suspensions by reflux pipetting. Single cell suspensions were prepared by cytocentrifugation, then stained for general morphology and insulin production. The foci contained cells producing the endocrine hormones glucagon (a cells), insulin ($\beta$ cells) and/or somatostatin ($\delta$ cells). Furthermore, the major population of cells stained positive with anti-insulin antibody, indicating the major cell type contained in the cultured IdI is an insulin-producing $\beta$ cell. FIGS. 1A through 1D show the various cell types which develop during the culture process. FIG. 2 shows a well-developed IdI obtained after the in vitro culture of cells according to the method of the subject invention.

EXAMPLE 2
Culturing of Human IdIs

For culturing human IdI cells, a procedure similar to that described in Example 1 was utilized. The procedure of the subject invention is particularly advantageous because it is not necessary to utilize fetal cells to initiate the cell culture. In a preferred embodiment, the human cells can be suspended in Click's EHAA medium (or the equivalent thereof) supplemented with normal human serum. Preferably, the concentration of normal human serum used in the medium is about 0.25%–1% in phases I and II, respectively, and 5% during subsequent phases. The cultures were left undisturbed with no re-feeding for several weeks (phase I). After about 4–5 weeks in culture, cell differentiation was initiated by re-feeding the cultures with Click's EHAA medium supplemented with normal human serum and glucose as described in Example 1. IdIs were subsequently collected and single cell suspensions prepared for further propagation as described in Example 1.

EXAMPLE 3
Implantation of in vitro Grown Islet Cells

To test the efficacy of these in vitro generated IdIs to reverse the complications of IDD, approximately 150–200 foci plus some ductal epithelium grown in vitro according to the method of the subject invention from pancreatic tissue of NOD mice were dislodged from the tissue culture flask by reflux pipetting. The cells were then implanted beneath the kidney capsule of syngeneic diabetic NOD mice maintained by daily insulin injections. Implantation was accomplished by puncturing the kidney capsule with a hypodermic needle, threading a thin capillary tube through the puncture site into the kidney, and injecting the islet foci and epithelium directly into the cortex region. The capillary tube was carefully withdrawn and the puncture site cauterized. The surgical incision of each implanted mouse was clamped until the skin showed signs of healing. The implanted mice were maintained on insulin injections for 4 days at the full daily dosage, and then for 2 days at the half daily dosage, after which the mice were completely weaned from further insulin treatment. Control animals consisted of diabetic NOD mice that did not receive an implant.

Figure 7:
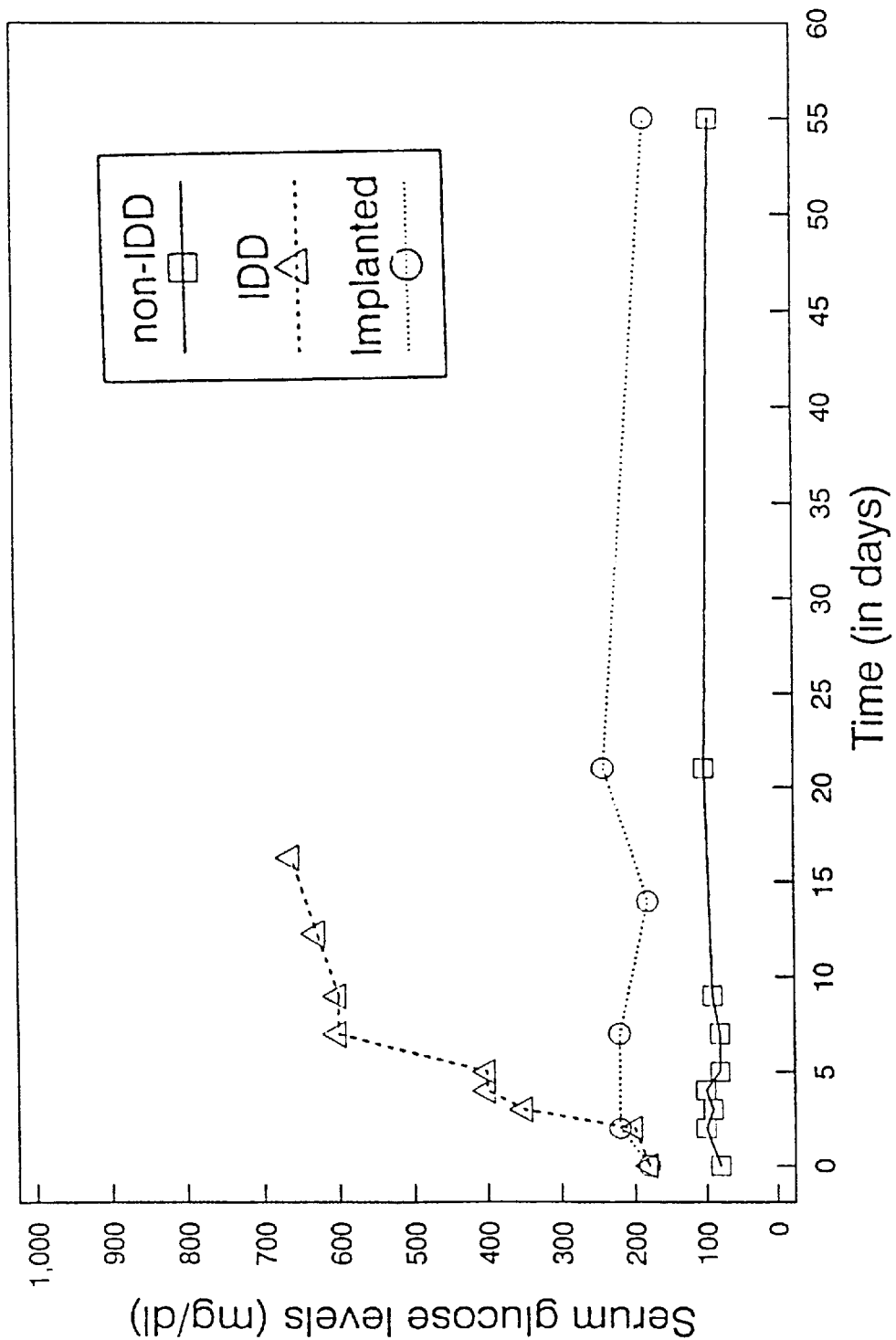
FIG. 7 shows data from control and implant NOD mice after cessation of insulin therapy.

Within 8–14 days after weaning from insulin, control NOD mice showed a rapid onset of overt disease, including lethargy, dyspnea, weight loss, increased blood glucose levels (400–800 mg/dl), wasting syndrome, failure of wound healing and death within 18–28 days (FIG. 7). Implanted NOD mice maintained a blood glucose level of about 180–220 mg/dl (which is slightly above the normal range for mice), showed increased activity, rapid healing of surgical and blood-draw sites, did not develop dyspnea, and remained healthy until killed up to 55 days post-implant for histological studies (FIG. 7). Similar observations have been seen with intra-splenic implants. These data are consistent with the concept that the implanted in vitro-generated IdIs and ductal epithelium provide the necessary insulin to maintain stable blood glucose levels over the time course of the experiment. The results of this study are published in Cornelius et al. (1997).

EXAMPLE 4
In vivo Production of an Ecto-Pancreatic Structure

Figure 8:
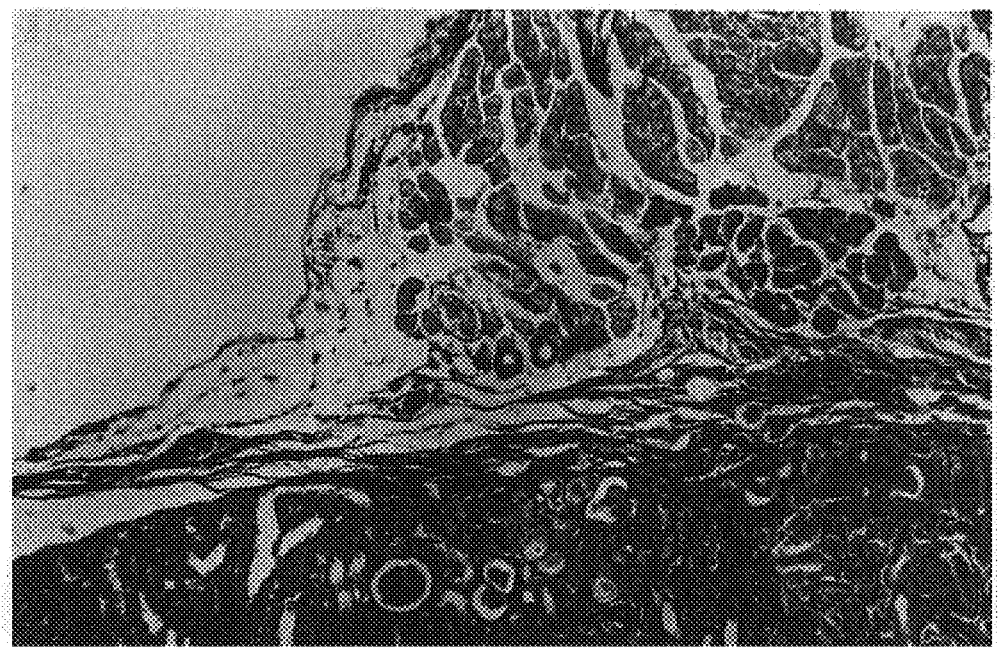
FIG. 8 shows an ecto-pancreatic structure.
Figure 8:
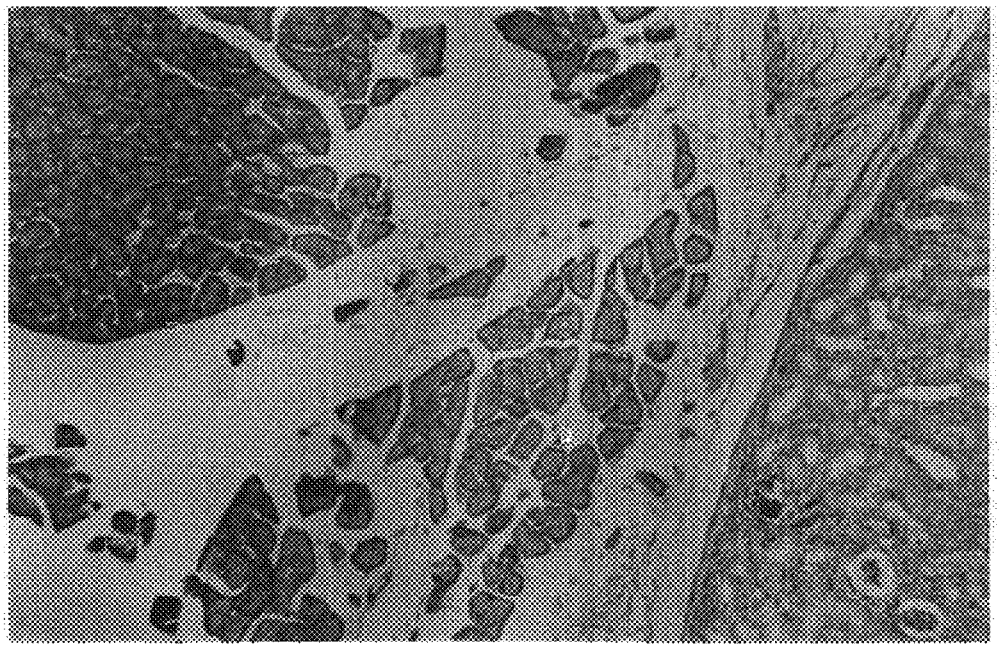

Histological examinations of the implant sites in mice that were implanted with the IdIs and epithelium as described in Example 3 revealed an additional characteristic of the in vitro generated IPSCs and/or IPCs. Implanted cells which "leaked" from the implant site of the kidney underwent additional proliferation and differentiation and formed a highly structured ecto-pancreatic structure. At first, the ecto-pancreatic structure consisted entirely of proliferating exocrine cells which organized into an exocrine tissue complete with innervating blood vessels. This exocrine tissue progressed to form islet-like endocrine structures (see FIG. 8). Thus, the in vitro cell cultures produced according to the methods of the subject invention contain IPSCs and/or IPCs capable of regenerating completely new exocrine and endocrine tissues. The growth of both exocrine and endocrine tissues provides new methods for treatment of pancreatic diseases, including pancreatitis and pancreatic cancer. However, in a preferred embodiment, the implanted material gives rise primarily to endocrine tissue and little or no exocrine tissue.

EXAMPLE 5
Long Term Propagation of IPSCs

Figure 6A:
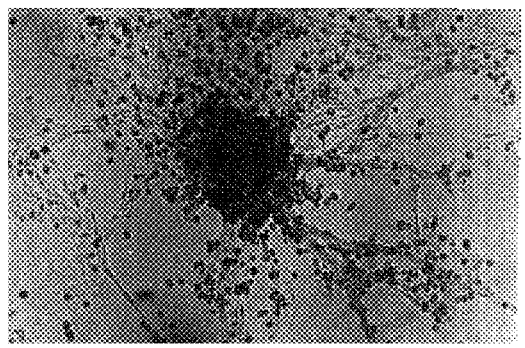
FIGS. 6A through 6F shows a series of micrographs in which an IdI, such as that shown in FIG. 3H, is harvested from a primary culture.
Figure 6B:
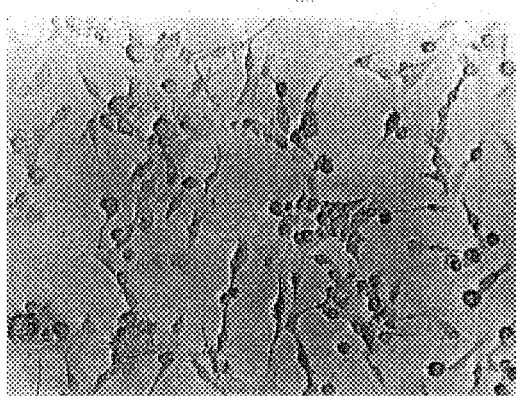
Figure 6E:
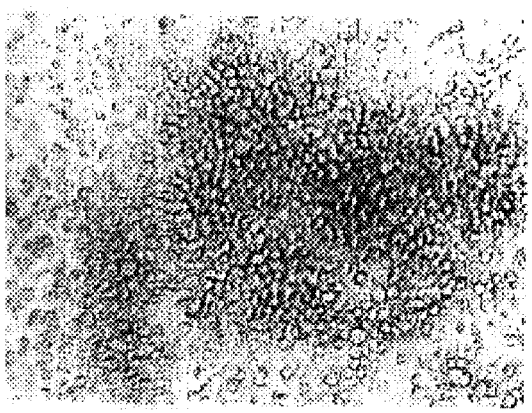
Figure 6C:
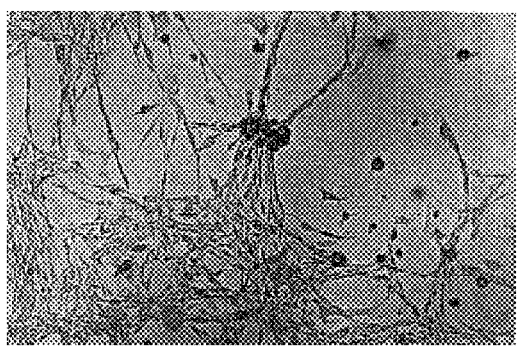
Figure 6F:
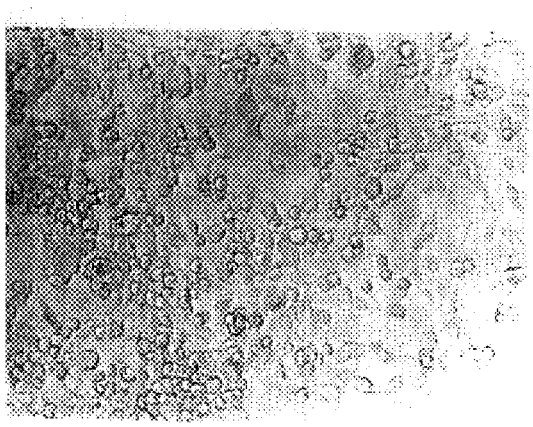
Figure 6D:
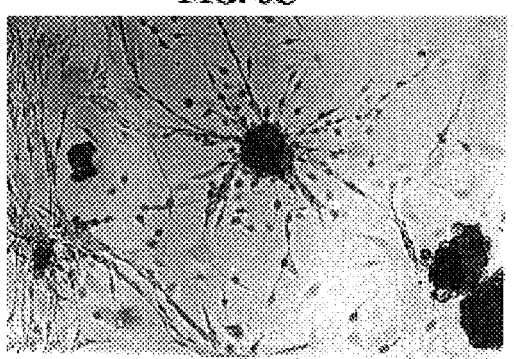

Long term propagation (>1 year) of the IPSCs was achieved through serial transfers of small numbers of the epithelium plus a few early-stage, proliferating IdIs to new culture flasks. Cells from a single 25 cm$^2$ tissue culture flask have been expanded successfully to 5–10 150 cm$^2$ tissue culture flasks. Interestingly, serial transfer uniformly resulted in the IdIs "melting" away, similar to the detached IdIs, while new epithelial monolayers formed (FIGS. 6A–6B). However, serially transferred cultures produced new IdIs far sooner than primary cultures and in higher number (as many as 200–250 structures per square inch of culture-FIGS. 6C–6D). However, eventually, after many rounds of serial growth and production of IdIs, a point is generally reached where after the IdI "melts", only differentiated cells proliferate (see FIGS. 6E-6F). The same thing can occur, in the absence of observable IdI formation, if primary pancreatic tissue is grown in primary culture under conditions which do not kill most of the differentiated cells. Generally, the IdIs can maintain their structural integrity up to 96 hours before melting or falling apart.

In subsequent serial transfer experiments, it has been found that long-term propagation that exceeds three years can be achieved.

EXAMPLE 6
Analysis of Islet-Like Structures

Photomicrographics of serial sections of immature, culture-generated IdIs and sections thereof (shown in FIGS. 4 and 5, respectively) again demonstrate the uniformity of growth. Large, somewhat differentiated cells which stain weakly with insulin are observed in the IdI center. Small differentiated cells which stained with glucagon were apparent at the periphery, while a significant number of immature, proliferating, and undifferentiated cells which did not stain with any of the endocrine hormone antibodies were present in the inner cortex. To determine more precisely the cell phenotypes present within the in vitro grown IdIs, the IdIs were collected following detachment from the epithelial monolayers, gently washed in medium, then broken into single cell suspensions by mechanical means, such as reflux pipetting in the presence of a proteolytic enzyme such as 0.25% trypsin. Slides of single cell suspensions were prepared by cytocentrifugation and stained for general morphology or cellular content. Several morphologically distinct mature and immature cell types are observed following H/E staining. Furthermore, individual cell populations stained with either anti-glucagon ($\alpha$ cells), anti-insulin ($\beta$ cells) or anti-somatostatin ($\delta$ cells) antibodies, indicating the pluripotent nature of the IPSCs giving rise to the IdIs. These observations emphasize two points: first, the weak staining for endocrine hormones suggests the cells of in vitro-generated IdIs remain relatively immature, and therefore capable of further differentiation upon in vivo implantation, and second, the fact that >100% of the cells could be accounted for by endocrine hormone staining indicates that some cells must express both glucagon and insulin simultaneously, which is considered a marker for immature cells that are on their way to end-stage differentiation (Teitelman et al., 1993).

EXAMPLE 7
Limiting Dilution of Pancreatic Cells—Cloning of Single IPSC

According to the methods described above, pancreatic tissue is dispersed in a culture medium. To isolate single IPSCs for clonal production of differentiated pancreatic cells, the dispersed pancreatic cells are subjected to limited dilution according to methods well known in the art. Thus, for example, serial ten-fold dilutions are conducted after an initial evaluation of the number of cells/mL in the dispersed sample, such that the final dilution yields, at the most, an average of 0.3 cells per microtiter well or other container suitable for this type of dilution experiment. Thereafter, the cells are allowed to remain undisturbed until IPSC/IdIs begin to develop. These progeny cells have each arisen from a single IPSC, and IPCs which can each be cultured to yield an IdI for implantation to form a pancreas-like structure.

EXAMPLE 8
Identification of Markers Associated with Different Stages of Pancreatic IPSC Differentiation, and Production of Antibody Molecules Specific to Each Stage of Differentiation Clusters of IPSCs produced according to Example 7 or by an analogous method are analyzed both prior to and after induction of differentiation according to Example 1 or by a similar method. The cells at each stage, from IPSC to fully committed differentiated pancreatic cells, are analyzed as follows:

A. Nucleic Acid: At each stage of differentiation, including the undifferentiated IPSC, IPC and the fully differentiated pancreatic cells, mRNA is isolated. This RNA is used to make cDNA according to standard methods known in the art (Maniatis et al., 1982) including but not limited to PCR dependent amplification methods using universal primers, such as poly A. Each amplification represents a library of message expressed at each stage of pancreatic stem cell development. Accordingly, message not present in IPSCs or IPCs but present in fully differentiated pancreatic cells is identified by hybridizing the cDNA from each stage and isolating message that remains unhybridized. Likewise, methods such as differential display PCR, or RDA-PCR (see above) may be used. In this manner, message unique to each stage is identified by subtraction of message present at other stages of differentiation. Antibodies, including monoclonal antibodies, are then produced by using these gene products as antigens according to methods well known in the art (see Goding, J. W., 1986). These antibodies are subsequently used to isolate cells from any given stage of differentiation based on affinity for markers expressed on the cell surface of the pancreatic cell. In addition, identification of specific markers which are expressed on the surface of the differentiated pancreatic cells allows production of knock-out lines of pancreatic cells by site-directed mutagenesis using the identified sequences to direct mutations in IPSCs or IPCs according to methods such as those disclosed in U.S. Pat. Nos. 5,286,632; 5,320,962; 5,342,761; and in WO 90/11354; WO 92/03917; WO 93/04169; and WO 95/17911. Selection of mutant cells which do not produce the knocked-out gene product is accomplished using the antibodies to the specific gene product selected against to provide clones of cells in which that product is absent.

B. Protein Markers: At each stage of differentiation, including the undifferentiated IPSCs, IPCs and the fully differentiated pancreatic cells, antibodies are generated to whole cells and subcellular fractions, according to standard methods known in the art. As specific examples of this process:

a) Production of rat anti-mouse IPSC mAbs: To enhance selection of B lymphocytes activated against IPSC-specific antigens, rats are immunized with normal mouse tissue followed by treatment with cyclophosphamide on day 7 post-immunization. Cyclophosphamide selectively kills the reactive B cells, leaving the rats unresponsive to normal mouse antigens. On day 14 post-immunization, the rats are re-challenged with cells collected from various stages of mouse IPSC cultures. Three to four weeks after this secondary challenge, the rats are re-immunized with IPSC culture cells for three days, then fused with the SPO/2 myeloma partner. Positively reacting antibodies are selected and cloned.

b) Production of mouse anti-human IPSC mAbs: Mouse anti-human IPSC mAbs are prepared using the same procedure as described above for the production of rat anti-mouse mAbs, except that mice are immunized with normal human tissue and then re-challenged after cyclophosphamide treatment with cells from various stages of human IPSC cultures.

c) Use of anti-IPSC mAbs in the identification of various differentiation stages of islet cell growth: The mAbs raised against IPSC cultured cells are used to sort by FACS or any other means known in the art, such as in magnetically stabilized fluidized beds (see below), the various cell populations defined by these reagents. Sorted cell populations are examined for their stages of differentiation (e.g., co-expression of insulin, glucagon, somatostatin, $\beta$-galactosidase, tyrosine hydroxylase, the Reg-gene to name a few) and their growth capacity (e.g., their ability to initiate IPSC cultures).

Reagents which define cell surface and differentiation marks of cells involved in the neogenesis of islets are useful for the scientific community in this area of research. In addition, such reagents greatly facilitate the isolation (or enrichment) of IPSCs per se. Isolation of IPSCs permits testing of the efficacy of re-implanting IPSCs instead of whole IdIs into IDD patients, or even implantation directly into the pancreas, circumventing the need for extra-pancreatic implants.

In addition, these antibodies are used to isolate cells from any given stage of differentiation based on affinity for markers expressed on the cell surface of the pancreatic cell. Identification of specific markers which are expressed on the surface of the differentiated pancreatic cells allows production of knock-out lines of pancreatic cells. Cells which do not produce the undesirable gene product are selected by using the antibodies to select for clones of cells in which that product is absent. In an analogous fashion, markers significant to T-cell recognition and destruction of differentiated pancreatic cells are identified by activating naive T-cells with whole pancreatic cells or subcellular fractions thereof, across the differentiation process. Identification of markers significant to T-cell activation allows subsequent modification of the IPSCs or IPCs to eliminate these markers and thereby produce cells which, in the differentiated state, are resistant to autoimmune destruction.

EXAMPLE 9

Isolation of Pancreatic Cells at Different Stages of Differentiation

Using the markers and ligand-binding molecules identified according to Example 8, pancreatic IPSCs, IPCs or partially or completely differentiated pancreatic cells can be isolated according to methods well known in the art. Accordingly, the methods for hematopoietic stem cell isolation disclosed in U.S. Pat. Nos. 5,061,620; 5,437,994; 5,399,493; in which populations of pure stem cells are isolated using antibodies to stem cell markers, are hereby incorporated by reference as if fully set forth herein. Likewise, the methods for mammalian cell separation from mixtures of cells using magnetically stabilized fluidized beds (MSFB), disclosed in U.S. Pat. No. 5,409,813, are hereby incorporated by reference as if fully set forth herein. Antibodies to markers identified at each stage of pancreatic IPSC differentiation are attached to magnetizable beads, and cells are passed through the magnetically stabilized fluidized bed. Cells which adhere to the antibody bound magnetizable beads, or cells which flow through the bed, are isolated.

Any of a number of other methods known in the art for isolation of specific cells may be used for this purpose. These methods include, but are not limited to, complement destruction of unwanted cells; cellular panning; immunoaffinity chromatography; elutriation; and soft agar isolation techniques (see Freshrey, R. I., 1988).

EXAMPLE 10

Analysis of Factors which Trigger Pancreatic IPSC Differentiation and Factors Produced at Different Stages of IPSC Differentiation Cells isolated according to the methods of Example 9 or like methods are cultured according to the method of Example 1 or like culturing method. Factors significant in inducing differentiation are assayed by adding different factors to the growth medium and observing the differentiation inducing effect on the cells. Thus, conditioned culture media from various cells can be tested, and factors which cause pancreatic IPSC differentiation are isolated using induction of differentiation as a purification assay. Other factors such as glucose, other chemicals, hormones and serum fractions are similarly tested to isolate the significant differentiation inducing factors.

Factors produced at different stages of differentiation are isolated and analyzed from the conditioned culture medium of cells at each stage of the differentiation process. These factors are likewise tested for their autocrine effect on IPSCs and further differentiation of partially differentiated cells.

EXAMPLE 11

Genetic Modification of Pancreatic IPSCs to Produce Autoantibody, CTL Resistant, and HLA Modified Differentiated Pancreatic Cells Pancreatic IPSCs or IPCs cultured according to Example 1 or 2 or isolated according to Example 8 are subjected to genetic modification according to any method known in the art to produce autoantibody and CTL resistant cells, according to methods such as those disclosed in U.S. Pat. Nos. 5,286,632; 5,320,962; 5,342,761; and in WO 90/11354; WO 92/03917; WO 93/04169; and WO 95/17911. Alternatively, selection of resistant IPSCs or IPCs is accomplished by culturing these cells in the presence of autoantibody or IDD associated CTLs or CTLs activated with IDD specific autoantigens. As a result of these techniques, cells having increased resistance to destruction by antibody or T-lymphocyte dependent mechanisms are generated. Such cells are implanted into an appropriate host in an appropriate tissue as disclosed above in Examples 3 and 4 to provide a pancreas-like structure which has increased resistance to destruction by autoimmune processes.

Likewise, the human leukocyte antigen profile of the pancreatic IPSC and differentiated cell is modified, optionally by an iterative process, in which the IPSC or IPC is exposed to normal, allogeneic lymphocytes, and surviving cells selected. Alternatively, a site directed mutagenesis approach is used to eliminate the HLA markers from the surface of the IPSC, IPC or differentiated cells, and new IPSCs or IPCs thereby generated are used to implant into a recipient mammal in need of such implantation.

In a specific example, the adeno-associated virus (AAV) vector system carrying the neomycin-resistance gene, neo is used. AAV can be used to transfect eukaryotic cells (Laface, 1988). In addition, the pBABE-bleo shuttle vector system carrying the phleomycin-resistance gene is used (Morgenstein, 1990). This shuttle vector can be used to transform human cells with useful genes as described herein.

a) Transfection of IPSCs: Cultured IPSCs or IPCs are transfected with either the retroviral segment of the pBABE-2-bleo vector by electroporation or the AAV-neo vector by direct infection. Adherent cells from established cultures are removed gently from the tissue culture flasks using C-PEG buffer (phosphate buffered saline supplemented with EDTA and high glucose). These cells are suspended in DMEM and 10% fetal rat serum containing the retroviral stock, and in the case of pBABE-bleo, subjected to electroporation. (Since electroporation can be a fairly harsh procedure compared to direct viral infection, the cells subject to electroporation are examined for viability. Viability of the cells is determined by their ability to exclude vital dye and analysis of injury-associated cell products such as glycosaminoglycans and hydroperoxides.) Secondary cultures of the transfected cells are established. Re-cultured cells are selected for resistance to phleomycin or neomycin, respectively.

b) Identification of pro-viral DNA in transformed cells: Neomycin or phleomycin resistant cultured cells are tested for the presence of the appropriate transfecting viral DNA. Cells are removed from the culture flasks using C-PEG buffer and digested in lysis buffer containing proteinase K. DNA is phenol/chloroform extracted, then precipitated in ethanol/sodium acetate. Proviral DNA is identified using nested PCR. For the first reaction, PCR primers are used which amplify the entire open reading frame of the appropriate resistance gene. For the second PCR reaction, the PCR product is used as template. Selected internal 5' and 3' primers are used which amplify an internal sequence of known base pair size. The final PCR product is detected by ethidium bromide staining of agarose gels following electrophoresis and/or probing of Southern blots.

c) Stability of transformation: The long-term stability of the transformations is determined by maintaining long-term growing cultures of the transfected cells and periodically testing them for the presence of pro-viral DNA, as described above.

These studies provide information on the efficacy and reproducibility of transfection procedures using IPSCs or IPCs as target cells. Furthermore, they establish a sound foundation for use of transformed IPSCs or IPCs in treating IDD patients.

EXAMPLE 12
Encapsulation of in vitro Generated IdIs and Implantation Into a Mammal Methods for encapsulation of cells are well known in the art (see, for example, Altman, et al., 1984, *Trans. Am. Soc. Art. Organs* 30:382–386, herein incorporated by reference, in which human insulinomas were enclosed in selectively permeable macrocapsules). Accordingly, isolated in vitro generated IdIs, optionally genetically modified according to Example 11, are encapsulated in an insulin, glucagon and somatostatin permeable encapsulant. Preferably such encapsulant is hypoallergenic, is easily and stably situated in a target tissue, and provides added protection to the implanted structure such that differentiation into a functional entity is assured without destruction of the differentiated cells.

Figure 12:
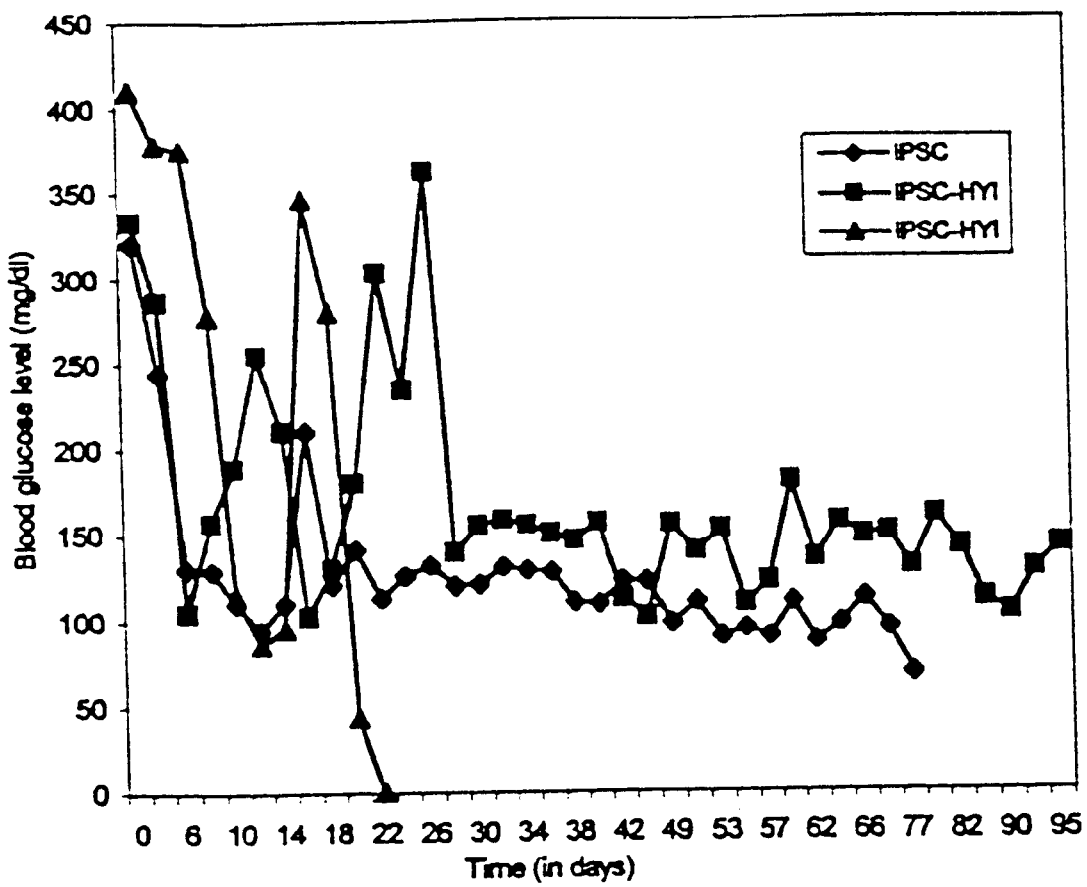
FIG. 12 illustrates the reversal of diabetes in diabetic NOD mice using subcutaneously implanted IdIs some of which have been encapsulated in hyaluronic acid.

As described in Examples 3 and 4, in vitro generated IdIs implanted under the kidney capsule can provide adequate insulin to maintain stable blood glucose levels over the time of experiment (see also Cornelius et al., 1997). In order to test another implantation site for diabetes reversal and also to investigate the potential of hyaluronic acid (generously supplied by Dr. Karl Arfors of Q Med of Scandinavia, San Diego, Calif.) as an encapsulating material, five thousand IdIs plus a small amount of contaminating ductal epithelium were implanted in a subcutaneous pocket on the right shoulder of 3 diabetic mice (blood glucose level~400 mg/dl) that were on insulin therapy. Since hyaluronic acid (a copolymer of D-glucuronic acid and N-acetyl-D-glucosamine) is a self molecule, it is considered to be immunologically safer. Two mice received the implants within 100 μl of hyaluronic acid gel (Q Med of Scandinavia), and one mouse received IdIs without the gel. Mice were weaned from insulin 2 days after implantation. On day 26 post implantation, a recipient of IdIs in hyaluronic acid died of hypoglycemia. In the other 2 mice, diabetes had been reversed and there was no evidence of autoimmune graft destruction as determined by stable blood glucose at near normal levels for 3 months (FIG. 12).

The procedure was as follows. Three 18–22 week old diabetic NOD/UF were maintained for 1 week prior to implantation on insulin (0.1 U/day). Their uncontrolled glucose excursion levels in the blood were between 350–430 mg/dl. Prior to implantation, mice were anesthetized using metaphane. After shaving the right upper shoulder area, a small incision was made which was then carefully dilated to a pocket with scissors. Five thousand IdIs were implanted into the subcutaneous pocket in 20 μl volume of HBSS. For encapsulation with hyaluronic acid, 100 μl of hyaluronic acid gel was first introduced into the pocket, and then carefully 20 μl of implant tissue was introduced into the gel. Immediately after implantation, the pocket was closed by clipping. Animals were kept under warm light till they recovered from anesthesia. Two days after implantation, they were weaned from insulin. Glucose levels were determined using glucose strips (Boehringer Mannheim, Indianapolis, Ind.) and glucose monitor AccuChek-EZ every $2^{nd}$ day at the same time point.

The absence of autoimmune destruction of non-encapsulated implants implies that the long-term in vitro growth of IPSCs could have reduced the antigenicity of IdIs. The hypoglycemia in the mouse that died could have been due to an excessive insulin secretion in vivo by IdIs, or uncontrolled growth and differentiation of IPSCs within the IdIs in vivo. In the treatment of IDD in humans, the risk of fatal hypoglycemia can be reduced by monitoring of patient serum glucose and/or insulin.

EXAMPLE 13
Differential Expression of REG-1, IPF-1 and Tyrosine Hydroxylase Genes in IPSCs and IdIs Islets associated with ductal structures were hand-picked from pancreatic tissue explanted from 19–20 week old prediabetic male NOD/Uf mice and partially digested with collagenese, as detailed elsewhere (Leiter et al., 1987). Upon culturing of trypsin-digested cell suspension in Earls high amino acid medium (EHAA) containing normal mouse serum (NMS), IPSCs, IPCs and IdIs were generated in vitro. Consistent with the results described in Examples 3 and 4 and in Cornelius et al. (1997), IdIs generally grew to a constant size (100–150μ) upon the epithelial monolayers and contained somewhat differentiated cells within the center of the IdIs that stained weakly for insulin and possibly for glucagon. While differentiated cells which stained strongly for glucagon were apparent at the periphery, a significant number of immature, proliferating, and undifferentiated cells which did not stain with any of the endocrine hormone antibodies were present in the inner cortex.

The expression of endocrine hormones by enriched IdIs and IPSCs was confirmed by detection of mRNA transcripts following RT-PCR. As presented in FIG. 9, mRNA transcripts of insulin I, insulin II, glucagon and somatostatin were detected in both populations of cells. Each population also expressed mRNA transcripts of insulin receptors, insulin-like growth factor I (IGF-I), IGF-II, hepatocyte growth factor (HGF) and its receptor C-MET (data not shown). We analyzed expression of mRNA transcripts of genes related to development and differentiation such as REG-1, IPF-1 (PDX-1), beta galactosidase, tyrosine hydroxylase, and beta 2/neuroD. The REG gene product belongs to a family of calcium-dependent (C-type) lectins and is known to induce islet β cell growth (Watanabe et al., 1994), and also may play a role in the induction of islet neogenesis from ductular precursors (Zenilman et al., 1996). During development, the entire early pancreatic rudiment and part of the surrounding gut tube expresses the homeobox gene IPF-1 (Guz et al., 1995), and in the absence of IPF-1 gene the embryos of the mutant mice completely lack a pancreas (Johnson et al., 1994). Both β-galactosidase and tyrosine hydroxylase enzymes are considered to be reliable markers for islet-forming precursors (Gu et al., 1993; Beattie et al., 1994). The transcription factor beta2/neuroD has been shown to be involved in the morphogenesis of islets and in the development of secretin and cholecystokinin producing enteroendocrine cells (Naya et al., 1997).

While IPSCs-expressed relatively more levels of REG-1 and IPF-1 gene transcripts there was no detectable expression of tyrosine hydroxylase mRNA within IdIs (FIG. 9). There was no difference in the levels of β-galactosidase and beta2/neuroD transcripts between these two cell populations.

The results illustrated in FIG. 9 were obtained as follows. Total RNA was prepared from IPSCs devoid of any IdIs, or IdIs using Trizol™ reagent (Life Technologies, Inc. Gaithersburg, Md.). All primers were designed based on sequences of open-reading frames obtained from GEN-BANK. MAPPing of the mRNA profiles using RT-PCR was performed according to protocols detailed by Anderson et al. (1993). PCR primers for the endocrine hormones, and growth/differentiation factors were purchased from Life Technologies, Inc. PCR products were size separated by gel electrophoresis in 1.2% agarose and transferred to nylon membranes by vacuum blotting and UV cross-linking. The specificity of the PCR amplifications were predetermined by hybridizations using internal sequence probes and the Genius calorimetric detection system of Boehringer Mannheim (Indianapolis, Ind.). When PCR products were not visible after amplification, hybridization data has been presented (e.g., tyrosine hydroxylase, IPF-1 and β-galactosidase).

These results are indicative of subtle changes that coincide with the formation of IdIs from IPSCs. Since we believe that progenitor cells are present within the IdIs through histological analysis (Cornelius et al., 1997) and since individual IdIs dissolve into IPSC and/or IPCs giving rise to more IdIs, it is not surprising to observe the expression of a precursor marker such as β-glactosidase by IdIs.

EXAMPLE 14
Enhancement of In vitro Proliferation of IPSCs by Different Sera

Figure 10:
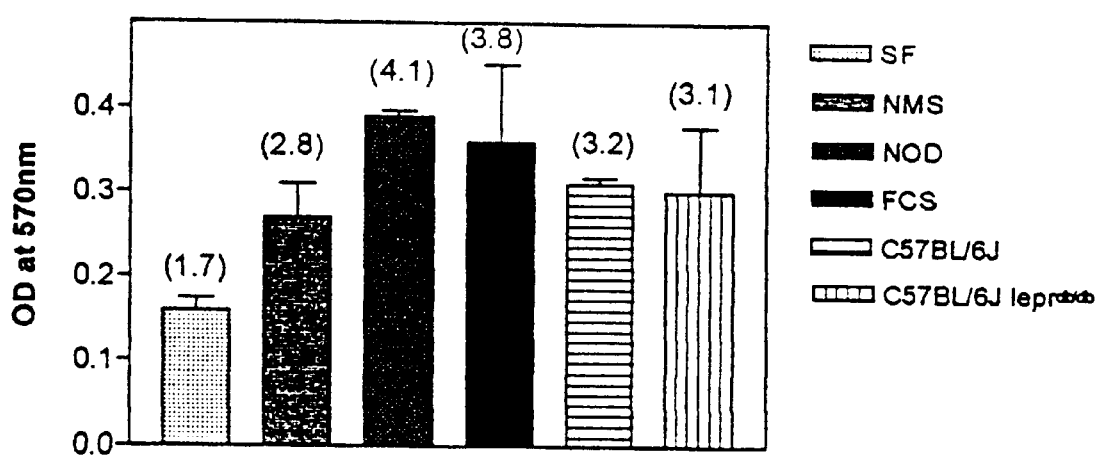
FIG. 10 illustrates the enhancement in in vitro proliferation of IPSCs upon exposure to various sera.

In our prior experiments, the cultures of IPSCs were typically maintained in EHAA medium containing 0.5% NMS. The differential effects of sera on the growth of IPSCs in vitro for 48 hours was determined using the MTT assay. Serum presence is essential for the growth of IPSCs. In the absence of serum (serum free or SF EHAA), cells detached from the flasks/tissue culture plates and died within 96 hours. Depending on the serum source, IPSCs increased between 2.8–4.1 fold in number within 48 hours upon glucose challenge (17.5 mM) (FIG. 10). NOD serum at 0.5% concentration appeared to be superior to other sera tested. We also investigated whether the serum from leptin receptor ($Lepr^{db/db}$) mutant mice on C57BL/6J background (Jackson Laboratories, ME) contains potential islet cell growth factors since these mice manifest hyperplasia of the islet β cells, hyperinsulinemia and elevated blood glucose. The $Lepr^{db/db}$ and C57Bl/6J sera were used at 0.5% level in EHAA medium. As shown in FIG. 10, there was no difference between $Lepr^{db/db}$ serum and control C57BL/6J serum. While all tested sera induced growth and IdI formation, there was no detectable in vitro insulin secretion upon glucose challenge (17.5 mM).

To measure IPSC proliferation, $2\times10^4$ IPSCs (viable cell number counted by trypan blue exclusion test) were seeded in 24 well tissue culture plates (Coastar, Cambridge, Mass.) in 2 ml of EHAA medium containing 0.5% of each indicated sera for 48 hrs. Three hours prior to the end of the culture period, 200 µl of water soluble MTT (Boehringer Mannheim, Indianapolis, Ind.) (stock of 5 mg/ml) was added to each well, and incubated for 3 hrs at 37° C. Immediately after incubation, the medium was removed and converted dye was solubilized with acidic isopropanol (0.1 N HCl in absolute isopropanol), and absorbance of the dye was measured at 570λ using Beckman DU640 spectrophotometer (Beckman, Fullerton, Calif.). The data in FIG. 10 is expressed as increase in cell number as determined from the standard MTT assay curves obtained by running simultaneously assays using known number of viable IPSCs. Comparisons between groups were done using one tailed t-test.

EXAMPLE 15
Induction of Insulin Production by in vitro Cultured IdIs Using Secretagogues Because in Example 15, none of the sera tested resulted in release of insulin upon glucose challenge, experiments were carried out to analyse the potential of nicotinamide to induce insulin production and release. Nicotinamide is a poly (ADP-ribose) synthetase inhibitor known to differentiate and increase the β cell mass in cultured human fetal pancreatic cells (Otonkoski et al., 1993). It also protects β cells from desensitization induced by prolonged high glucose environment (Ohgawara et al., 1993), stimulates β cell replication in vivo in mouse pancreas (Sandler et al, 1988), and prevents diabetes in NOD mice (Pozzilli et al., 1993). There are a number of plausible mechanisms by which nicotinamide may be beneficial in preventing β cell destruction: by returning the β cell content of adenine dinucleotide (NAD) toward normal by inhibiting poly ADP-ribose polymerase (Inoue et al., 1989); by serving as a free-radical scavenger, and/or by inhibiting cytokine induced islet nitric oxide production (Cetkovic-Cvrlje et al., 1993). Nicotinamide has been used in several studies that included new-onset diabetes patients. The results have been mixed, with some studies showing marginal beneficial effects of nicotinamide and others being without effect (Vague et al., 1987; Vague et al., 1989; Mendola et al., 1989; Lewis et al., 1992; Viallettes et al., 1990).

Figure 11:
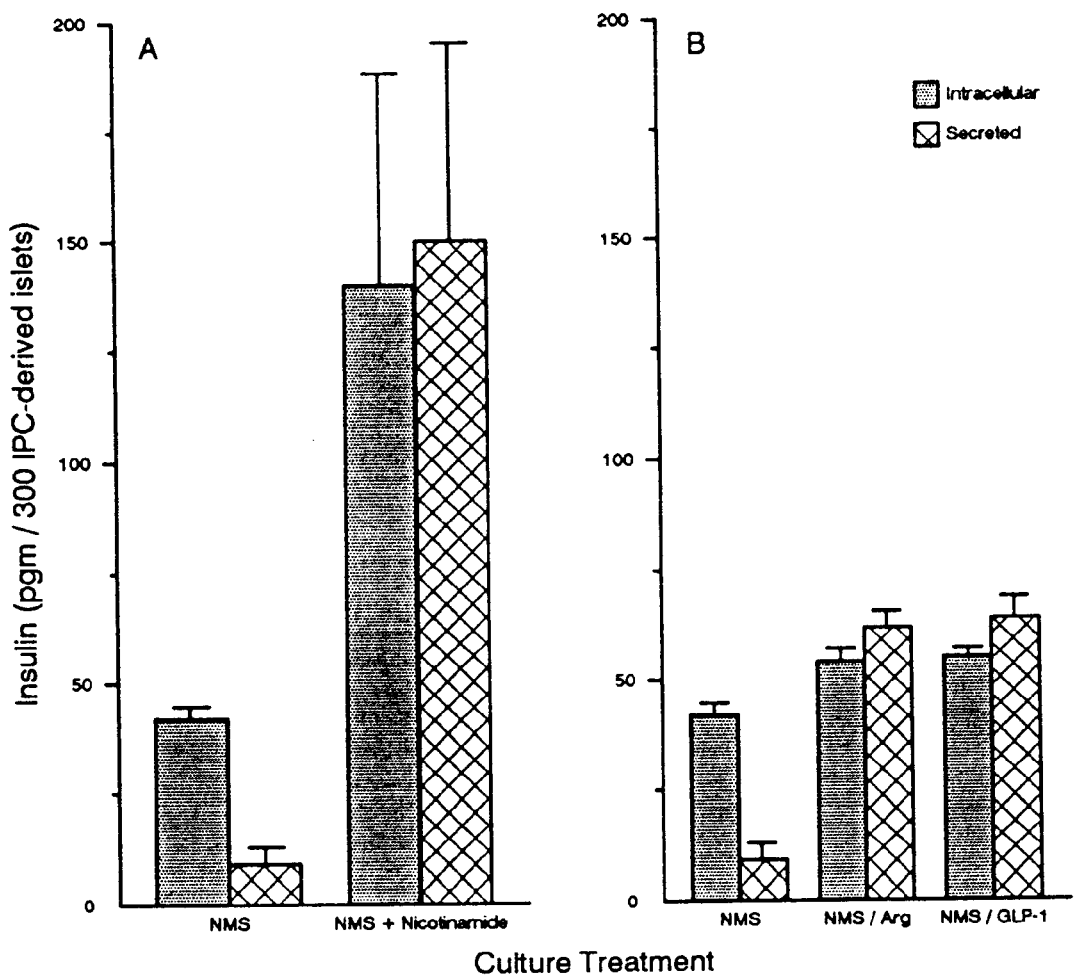
FIG. 11A illustrates the induction of insulin production in IdIs by nicotinamide.
FIG. 11B shows how secretagogues arginine and GLP-1 induce release of intracellular insulin in IdIs.

To determine insulin secretion, 300 IdIs derived from NOD/Uf pancreatic IPSCs were cultured in vitro for 5 days in EHAA medium containing either 0.5% NMS or prediabetic NOD mouse serum with or without nicotinamide (1–10 mM). At the end of the culture period, cells were washed twice in Krebs ringer buffer (KRB) and stimulated with 17.5 mM glucose in KRB for 3 hours. As shown in FIG. 11A, nicotinamide-treated islets possessed increased insulin content and secreted significantly increased levels of insulin compared to cultures with glucose alone ($P<0.05$). Secretogogues, e.g., arginine, which stimulates islet β cells through voltage dependent $Ca^{2+}$ channels, and glucagon like peptide-1 (GLP-1), which stimulates β cells through the elevation of cAMP and the protein kinase A pathway, in conjunction with 17.5 mM glucose, also induced insulin release from the IPC-derived islets, but to a lesser degree than nicotinamide (FIG. 11B). Nicotinamide, in combination with various growth factors, also induced the differentiation of IPCs to islets.

The data illustrated in FIGS. 11A and 11B were obtained as follows. Three hundred IdIs (from culture flasks containing EHAA-0.5% NMS medium) were seeded in 24 well plates in 2 ml of EHAA medium containing 0.5% of NMS with or without nicotinamide (1–10 mM) for 5 days at 37° C. (5% $CO_2$). For secretagogues, IdIs were cultured in EHAA-0.5% NMS medium for 5 days. Three hours prior to the end of the incubation period, medium was removed and IdIs gently washed twice with KRB. To stimulate insulin secretion, 17.5 mM glucose was added to wells in 1 ml of KRB, and incubated at 37° C. for 3 hrs. Following incubation, culture supernatants were stored at 70° C. until use. The IdIs in each well were then subjected to 1 ml of ice-cold acid-ethanol extraction overnight at 4° C., and cell-free extracts were neutralized with Tris base (400 mM final concentration) prior to storing at −70° C. until use. To test the effect of secretagogues, 10 mM arginine and 1 nM GLP-1 (Sigma Chemicals, St Louis, Mo.) were used for the final 3 hours incubation in KRB. The insulin in the supernatants and in the extract were determined using an insulin ELISA kit (Crystal Chemical Inc., Chicago, Ill.), with rat insulin standard for quantitation (supplied in the kit). Comparisons between groups were done using the one tailed t-test.

Taken together, these results indicate the potential of IPSC derived IdIs to mature/differentiate to a degree that insulin production could be induced in vitro in the presence of nicotinamide.

It should be understood that the examples and embodiments described herein are for illustrative purposes only and that various modifications or changes in light thereof will be suggested to persons skilled in the art and are to be included within the spirit and purview of this application and the scope of the appended claims.

REFERENCES

Eisenbarth, G. S., (1986) *N. Engl. J. Med.* 314:1360.
Cahil, G. F., and H. O. McDevitt (1981) *N. Engl. J. Med.* 304:1454.
Todd J A, J. A., et al. (1989) *Nature* 338:587.
Prochazka, M., D. V. Serreze, S. M. Worthen, and E. H. Leiter (1989) *Diabetes* 38:1446.
Baekkeskov, S., et al., (1982) *Nature* 298:167.
Baekkeskov, S., et al. (1990) *Nature* 347:151.
Reddy, S., N. J. Bibby, and R. B. Elliot (1988) *Diabetologia* 31:322.
Pontesilli, O., P. Carotenuto, L. S. Gazda, P. F. Pratt, and S. J. Prowse (1987) *Clin. Exp. Immunol.* 70:84.
Wang, Y., L. Hao, R. G. Gill, and K. J. Lafferty (1987) *Diabetes* 36:535.
Karjalainen et al. (1992) *N. Engl. J. Med.* 327:302.
Serreze, D. V., E. H. Leiter, E. L. Kuff, P. Jardieu, and K. Ishizaka (1988) *Diabetes* 37:351
Signore, A., P. Pozzilli, E. A. M. Gale, D. Andreani, and P. C. L. Beverly (1989) *Biabetologia* 32:282.
Jarpe, A. J., M. Hickman, J. T. Anderson, W. E. Winter, and A. B. Peck (1991) *Regional Immunol.* 3:305
Bendelac, A., C. Carnaud, C. Boitard, and J. F. Bach (1987) *J. Exp. Med* 166:823.
Gazdar et al. (1980) *P.N.A.S.* 77(6):3519–3525.
Brothers, A. J., PCT Application WO 93/00441, published Jan. 7, 1993.
Korsgren et al. (1993) *J. Med. Sci.* 98(1):39–52.
Nielson, J. H., PCT Application WO 86/01530, published Mar. 13, 1986.
McEvoy et al. (1982) *Endocrinol.* 111(5):1568–1575.
Zayas et al., EPO 0 363 125, published Apr. 11, 1990.
Coon et al., PCT Application WO 94/23572, published Oct. 27, 1994.
Miller, B. J., M. C. Appel, J. J. O'Neil, and L. S. Wicker (1988) *J. Immunol.* 140:52.
Hanafusa T. et al. (1988) *Diabetes* 37:204.
Bendelac A. et al. (1988) *J. Immunol.* 141:2625.
Rossini, A. A., J. P. Mordes, and E. S. Handler (1988) *Diabetes* 37:257.
Nerup, J., et al. (1989) *Diabetes Care* 11:16.
Kanazawa, Y., et al. (1984) *Diabetologia* 27:113.
Anderson, J. T., J. G. Cornelius, A. J. Jarpe, W. E. Winter and A. B. Peck (1993) *Autoimmunity* 15:113.
Shieh, D. C., J. G. Cornelius, W. E. Winter, and A. B. Peck (1993) *Autoimmunity* 15:123.
Peck, A. B. and F. H. Bach (1973) *J. Immunol. Methods* 3:147.
Peck, A. B. and R. E. Click (1973) *European J. Immunology* 3:382.
Lacey, P. E., J. Davies (1957) *Diabetes* 6:354.
Baum, J., B. E. Simons, R. H. Unger, L. L. Madison (1962) *Diabetes* 11:371.
Dubois, M. P. (1975) *P.N.A.S.* (USA) 72:1340.
Pelletier, G., R. Leclerc, A. Arimua, A. V. Schally (1975) *J. Histochem, Cytochem.* 23:699.
Larsson, L. I., F. Sundler, R. Hakanson (1975) *Cell Tissue Res.* 156:167.
Brelje, T. C., D. W. Scharp, R. L. Sorenson (1989) *Diabetes* 38:808.
Pictet, R. L., W. J. Rutter (1972) in *Handbook of Physiology*, D. Steiner and N. Frienkel, eds., (Williams & Wilkins, Baltimore, Md.) pp. 25–66.
Hellerstrom, C. (1984) *Diabetologia* 26:393.
Weir, G. C., S. Bonner-Weir (1990) *J. Clin. Invest.* 85:983.
Teitelman, G., S. Alpert, J. M. Polak, A. Martinez, D. Hanahan (1993) *Development* 118:1031.
Beattie, G. M., et al. (1994) *J. Clin. Endo. Med.* 78:1232.
Bonner-Weir, S., L. Orci (1982) *Diabetes* 41:93.
Teitelman, G., S. Alpert, D. Hanahan (1988) *Cell* 52:97.
Menger, M. D., P. Vajkoczy, C. Berger, K. Messmer (1994) *J. Clin. Invest.* 93:2280.
Eisenbarth, G. S. (1986) *N. Engl. J. Med.* 314:1360.
Leiter, E. H., M. Prochazka, D. L. Coleman (1987) *Am. J. Path.* 128:380.
Bonner-Weir S., F. E. Smith (1994) *T.E.M* 5:60.
Swenne, I. (1992) *Diabetologia* 35:193.
Hellerstrom, C., I. Swenne, A. Andersson (1988) in *The Pathology of the Endocrine Pancreas in Diabetes*, P. J. Lefebvre and D. G. Pipeleers, eds. (Springer-Verlag, Heidelberg, Germany) pp. 141–170.
Bonner-Weir, S., D. Deery, J. L. Leahy, G. C. Weir (1989) *Diabetes* 38:49.
Marynissen, G., L. Aerts, F. A. Van Assche (1983) *J. Develop. Physiol.* 5:373.
Neilsen, J. H., et al. (1992) *Adv. Exp. Med. Biol.* 321:9.
Brelje, T. C., et al. (1993) *Endocrinology* 132:879.
Weaver, C. V., R. L. Sorenson, H. C. Kuang (1985) *Diabetologia* 28:781.
Gu, D., and N. Sarvetnick (1993) *Development* 118:33.
Bonner-Weir, S., L. A. Baxter, G. T. Schuppin, F. E. Smith (1993) *Diabetes* 42:1715.
Rosenberg, L., A. I. Vinik (1992) *Adv. Exp. Med. Biol.* 321:95.
Otonkoski, T., et al. (1994) *Diabetes* 43:947.
Watanabe, T., et al., (1994) *P.N.A.S.* (USA) 91:3589.
Otonkoski, T., M. I. Mally, A. Hayek (1994) *Diabetes* 43:1164.
Payton et al. (1995) *J. Clin. Invest.* 96:1506–1511.
Jones, U.S. Pat. No. 5,286,632, issued Feb. 15, 1994.
Stiles, et al., U.S. Pat. No. 5,320,962, issued Jun. 14, 1994.
Mcleod, U.S. Pat. No. 5,342,761, issued Aug. 30, 1994.
Almond, PCT Application WO 90/11354, published Oct. 4, 1990.
Kay, et al., PCT Application WO 92/03917, published Mar. 19, 1992.
Berns, et al., PCT Application WO 93/04169, published Mar. 4, 1993.
Kucherlapti, et al., PCT Application WO 95/17911, published Jul. 6, 1995.

Durinovic, B. I., et al. (1994) *Diabetes* 43(11):1318–1325.
Elias and Cohen (1994) *Lancet* 343(8899):704–706.
Conrod et al. (1994) *Nature* 371(6495):351–385.
Santamaria et al. (1994) *Diabetes* 43(4):599–606.
Wegmann et al. (1993) *J. Autoimm.* 6(5):517–527.
Liang et al. (1992) *Science* 257:967–971.
Welsh et al. (1992) *Nuc. Acid. Res.* 20:4965–4970.
Lisitsyn (1993) *Science* 259:946–951.
Altman et al. (1994) *Trans. Am. Soc. Art. Organs* 30:382–386.
Maniatis et al. (1982) *Cold Spring Harbor.*
Goding, J. W. (1986) "Monoclonal Antibodies: Principles and Practice", *Academic Press.*
Tsukamato, et al., U.S. Pat. No. 5,061,620, issued Oct. 29, 1991.
Emerson, et al., U.S. Pat. No. 5,437,994, issued Aug. 1, 1995.
Emerson, et al., U.S. Pat. No. 5,399,493, issued Mar. 21, 1995.
Freshrey, R. I. (1988) *Animal Cell Culture* 198, IRL Press.
Anderson, J. T., J. G. Cornelius, A. J. Jarpe, W. E. Winter, A. B. Peck (1993) *Autoimmunity* 15:113.
Peck, A. B., R. E. Click (1973) *Eur. J. Immunol.* 3:875.
Peck, A. B., R. E. Click (1973) *Eur. J. Immunol.* 3:385.
Teitelman, G., S. Alpert, J. M. Polak, A. Martinez, D. Hanahan (1993) *Development* 118:1031.
Otonkoski, T., M. Knip, I. Wong, O. Simell (1991) *Life Sciences* 48:2157.
Marchetti, P., et al. (1994) *Diabetes* 43:827.
Otonkoski, T., G. M. Beattie, M. I. Mally, C. Ricordi, A. Hayek (1994) *J. Clin. Endo. Met* 78:1232.
Laface, D., P. Hermonat, E. K. Wakeland, A. B. Peck (1988) "Gene transfer into hematopoietic progenitor cells mediated by an adeno-associated virus vector," *Virology* 162:483–486.
Morgenstein, J. P., H. Land (1990) "Advanced mammalian gene transfer: high titre retroviral vectors with multiple drug selection markers and a complementary helper-free packaging cell line," *Nucleic Acids Res.* 18:3587–3596.
Cornelius, J. G. et al., *Horm. Metab. Res.* 29:271 (1997).
Zenilman, M. E. et al., *Surgery* 119:576 (1996).
Guz, Y. et al., *Development* 121:11 (1995).
Johnson, J. et al., *Nature* 371:606 (1994).
Naya, F. J. et al., *Genes Dev.* 11: 2323 (1997).
Otonkoski, T. et al., *J. Clin. Invest.* 92:1459 (1993).
Ohgawara, H. et al., *Tohoku. J. Exp. Med.* 169:159 (1993).
Pozzilli, P. and D. Andreani, *Diabetes Metabol. Rev.* 9:219 (1993).
Inoue, C. etal., *J. Biol. Chem.* 264:4747 (1989).
Cetkovic-Cvrlje, M., S. Sandler, D. L. Eizirik, *Endocrinology* 133:1739 (1993).
Vague, P. et al., *Lancet* 1:619 (1987).
Vague, P. et al., *Diabetologia* 32:316 (1989).
Mendola, G. et al., *Diabetologia* 32:160 (1989).
Lewis, M. C. et al., *Diabetes Care* 15:121 (1992).
Viallettes, B. et al., *Diabetic Med.* 7:731 (1990).
Sener, A. et al., *Diab. Res.* 13:157 (1990).
D. J. Drucker et al., *Proc. Natl. Acad. Sci. USA.* 84:3434 (1987).
The Diabetes Control and Complications Trial Research Group, *N. Engl. J. Med.* 329:977 (1993).
Fioretto, P. et al., *N. Engl. J. Med.* 339:69 (1998).
Weber, C. J. et al., *Cell Transplant.* 6:505 (1997).
Bach, F. H. et al., *Nat. Med.* 4:141 (1998).
Anderson, J. T. et al., *Autoimmunity* 15:113 (1993).
American diabetes association, professional section quarterly, summer 1998

What is claimed is:

1. A method of treating pancreatic disease in a mammal which comprises:

culturing pancreatic cells from a mammalian species in vitro under conditions that are favorable to the survival of islet-producing stem cells (IPSCs) and ductal epithelial cells, and substantially lethal to differentiated cells, whereby a composition comprising a ductal epithelial monolayer containing IPSCs is produced, and implanting the IPSC composition into a tissue of the mammal whereby treatment is effected.

2. The method of claim 1 wherein said IPSCs are encapsulated in an insulin, glucagon and somatostatin permeable capsule.

3. The method of claim 2 wherein said capsule comprises hyaluronic acid.

4. The method of claim 1 wherein the IPSCs originate from an individual into whom the IPSCs are implanted.

5. The method of claim 1 wherein the pancreatic disease is insulin-dependent diabetes.

6. The method of claim 1, wherein said conditions that are favorable to the survival of IPSCs and ductal epithelial cells and substantially lethal to differentiated cells, comprise a culture medium comprising little or no glucose, and low serum.

7. The method of claim 6 wherein said glucose concentration is less than about 1 mM and the serum concentration is less than about 0.5%.

8. A composition comprising islet producing stem cells (IPSCs) wherein the IPSCs are encapsulated in hyaluronic acid, and wherein the IPSCs are produced according to a method comprising the step of:

culturing pancreatic cells from a mammalian species in vitro under conditions that are favorable to the survival of IPSCs and ductal epithelial cells, and substantially lethal to differentiated cells, whereby a ductal epithelial monolayer containing IPSCs is produced.

9. The method of claim 8, wherein said conditions that are favorable to the survival of IPSCs and ductal epithelial cells and substantially lethal to differentiated cells, comprise a culture medium comprising little or no glucose, and low serum.

10. The method of claim 9 wherein said glucose concentration is less than about 1 mM and the serum concentration is less than about 0.5%.

11. A method of treating pancreatic disease in a mammal which comprises the steps of:

a) culturing pancreatic cells from a mammalian species in vitro under conditions that are favorable to the survival of IPSCs and ductal epithelial cells, and substantially lethal to differentiated cells, whereby a ductal epithelial monolayer containing IPSCs is produced, b) optionally initiating cellular differentiation, whereby IPCs and IdIs are produced, c) implanting in a mammal a composition comprising cells or tissue selected from the group consisting of said ductal epithelium, IPSCs, IPCs, IdIs and any combination thereof, whereby islet hormones are produced, providing for the treatment of the pancreatic disease.

12. The method of claim 11 wherein said composition is encapsulated before said implantation step.

13. The method of claim 11 wherein said implantation step comprises implanting into the mammal's pancreatic tissue.

14. The method of claim 11 wherein said implantation step comprises implanting into a subcutaneous pocket of the mammal.

15. The method of claim 11 wherein said implantation step comprises implanting beneath a kidney capsule in the mammal.

16. The method of claim 11, wherein the implanted composition comprises IPSCs.

17. The method of claim 11, wherein said conditions that are favorable to the survival of IPSCs and ductal epithelial cells and substantially lethal to differentiated cells, comprise a culture medium comprising little or no glucose, and low serum.

18. The method of claim 17, wherein said glucose concentration is less than about 1 mM and the serum concentration is less than about 0.5%.

* * * * *

UNITED STATES PATENT AND TRADEMARK OFFICE
CERTIFICATE OF CORRECTION

PATENT NO. : 6,703,017 B1
DATED : March 9, 2004
INVENTOR(S) : Peck et al.

It is certified that error appears in the above-identified patent and that said Letters Patent is hereby corrected as shown below:

Title page,
Item [56], References Cited, FOREIGN PATENT DOCUMENTS, please add the following reference:
-- WO WO95/29988 11/1995 --.
OTHER PUBLICATIONS, "Madesen et al." reference, the word "Endocrinoology" should read -- Endocrinology --.
"Korsgren" reference, the word "Upsala", should read -- Uppsala --.
Add the following references:
-- Cornelius et al. (1997) Horm. Metab. Res. 29:271-277.
Peck et al. (2001) Ann. Med. 33:186-192.
Pipeleers et al. (1991) Diabetes 40:908-919.
Ramiya et al. Nature Medicine 6:278-282.
Peck et al. Diabetes, Abstract Book, 55th Annual Mtg. and Scientific Sessions, 44 no. Supp.1, 10-13 June 1995, p. A10. --

Column 3,
Line 40, the letter "a" should be replaced with -- alpha --.

Column 7,
Line 60, "Idis" should read -- Idls --.

Column 8,
Lines 8, 15, 26 and 59, each occurrence of "Idis" should read -- Idls --.

Column 10,
Line 25, the word "supemates" should read -- supernates --.

Column 11,
Line 37, "Idis" should read -- Idls --.

Column 14,
Line 16, the word "quantitated" should read -- quantified --.
Line 58, "Idis" should read -- Idls --.

Column 26,
Line 17, the word "analyse" should be spelled -- analyze --.

UNITED STATES PATENT AND TRADEMARK OFFICE
CERTIFICATE OF CORRECTION

PATENT NO.    : 6,703,017 B1
DATED         : March 9, 2004
INVENTOR(S)   : Peck et al.

It is certified that error appears in the above-identified patent and that said Letters Patent is hereby corrected as shown below:

<u>Column 27,</u>
Line 12, the word "quantitation" should read -- quantification --.

Signed and Sealed this

Twenty-first Day of December, 2004

JON W. DUDAS
*Director of the United States Patent and Trademark Office*